(12) United States Patent
Rubinstein et al.

(10) Patent No.: US 7,474,906 B2
(45) Date of Patent: Jan. 6, 2009

(54) METHOD FOR DYE INJECTION FOR THE TRANSCUTANEOUS MEASUREMENT OF CARDIAC OUTPUT

(75) Inventors: Eduardo H. Rubinstein, Los Angeles, CA (US); Daniel P. Holschneider, Los Angeles, CA (US); Jean-Michel I. Maarek, Rancho Palos Verdes, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 0 days.

(21) Appl. No.: 11/744,147

(22) Filed: May 3, 2007

(65) Prior Publication Data

US 2008/0004511 A1      Jan. 3, 2008

Related U.S. Application Data

(63) Continuation-in-part of application No. 10/847,480, filed on May 17, 2004, which is a continuation of application No. 10/153,387, filed on May 21, 2002, now Pat. No. 6,757,554.

(60) Provisional application No. 60/747,401, filed on May 16, 2006, provisional application No. 60/292,580, filed on May 22, 2001.

(51) Int. Cl.
*A61B 5/00* (2006.01)
*A61B 5/02* (2006.01)
(52) U.S. Cl. .................... 600/317; 600/481
(58) Field of Classification Search ............... 600/476, 600/526, 431, 433, 435, 317, 420, 310, 504, 600/318, 479, 321, 410; 250/459.1; 424/440; 514/536, 817; 604/27, 30, 31, 34, 67, 250, 604/284; 128/DIG. 12; 137/512, 855; 417/474
See application file for complete search history.

(56) References Cited

U.S. PATENT DOCUMENTS

| 3,618,591 | A | 11/1971 | Bradley et al. |
| 4,109,647 | A | 8/1978 | Stern et al. |
| 4,303,336 | A | 12/1981 | Cullis |

(Continued)

FOREIGN PATENT DOCUMENTS

WO       WO 93/22670       11/1993

(Continued)

OTHER PUBLICATIONS

Darovic, G.O. Hemodynamic monitoring. Chapter 11: Monitoring cardiac output. 1995. pp. 327-346. 2d Ed. W.B. Saunders.

(Continued)

*Primary Examiner*—Max Hindenburg
*Assistant Examiner*—Brian Szmal
(74) *Attorney, Agent, or Firm*—McDermott Will & Emery LLP

(57) ABSTRACT

A system for evaluating the cardiovascular system parameters using indicator dilution and non-invasive or minimally invasive detection and calibration methods are disclosed. Intravascular indicators are stimulated, and emissions patterns detected for computation of cardiac output, cardiac index, blood volume and other indicators of cardiovascular health.

13 Claims, 12 Drawing Sheets

U.S. PATENT DOCUMENTS

| | | | | |
|---|---|---|---|---|
| 4,398,908 A * | 8/1983 | Siposz | | 604/31 |
| 4,730,622 A | 3/1988 | Cohen | | |
| 5,217,456 A | 6/1993 | Narciso, Jr. | | |
| 5,331,958 A | 7/1994 | Oppenheimer | | |
| 5,515,851 A * | 5/1996 | Goldstein | | 600/431 |
| 5,685,989 A | 11/1997 | Krivitski et al. | | |
| 5,687,726 A | 11/1997 | Hoeft | | |
| 5,766,125 A | 6/1998 | Aoyagi et al. | | |
| 5,797,396 A | 8/1998 | Geiser et al. | | |
| 5,830,365 A | 11/1998 | Schneditz | | |
| 5,999,841 A | 12/1999 | Aoyagi et al. | | |
| 6,041,246 A | 3/2000 | Krivitski et al. | | |
| 6,103,257 A * | 8/2000 | Nisonoff | | 424/440 |
| 6,155,984 A * | 12/2000 | Krivitski | | 600/526 |
| 6,159,445 A | 12/2000 | Klaveness et al. | | |
| 6,178,340 B1 | 1/2001 | Svetliza | | |
| 6,219,566 B1 | 4/2001 | Weersink et al. | | |
| 6,223,069 B1 | 4/2001 | Pfeiffer et al. | | |
| 6,228,344 B1 | 5/2001 | Donshow et al. | | |
| 6,230,035 B1 | 5/2001 | Aoyagi et al. | | |
| 6,280,386 B1 | 8/2001 | Alfano et al. | | |
| 6,280,703 B1 | 8/2001 | Combs et al. | | |
| 6,299,583 B1 | 10/2001 | Eggers et al. | | |
| 6,351,663 B1 * | 2/2002 | Flower et al. | | 600/476 |
| 6,424,857 B1 | 7/2002 | Henrichs et al. | | |
| 6,493,567 B1 | 12/2002 | Krivitski et al. | | |
| 6,542,769 B2 | 4/2003 | Schwamm et al. | | |
| 6,554,775 B1 | 4/2003 | Peyman et al. | | |
| 6,577,884 B1 | 6/2003 | Boas | | |
| 6,597,939 B1 | 7/2003 | Lampotang et al. | | |
| 6,718,190 B2 | 4/2004 | Krivitski et al. | | |
| 6,746,407 B2 | 6/2004 | Steuer et al. | | |
| 6,746,408 B2 | 6/2004 | Krivitski et al. | | |
| 6,746,415 B1 | 6/2004 | Steuer et al. | | |
| 6,986,744 B1 | 1/2006 | Krivitski | | |
| 7,261,696 B2 | 8/2007 | Krivitski | | |
| 2002/0151774 A1 | 10/2002 | Soller et al. | | |
| 2004/0156782 A1 | 8/2004 | Alum et al. | | |
| 2005/0182434 A1 | 8/2005 | Docherty et al. | | |

FOREIGN PATENT DOCUMENTS

WO    WO 2006/039731 A1    4/2006

OTHER PUBLICATIONS

Desmettre, T. et al. Fluorescence properties and metabolic features on indocyanine green (ICG) as related to angiography. Survey of opthalmology. Jul.-Aug. 2000. pp. 15-27. vol. 45, No. 1.

Diamond, et al. Quantification of fluorophore concentration in tissue-simulating media by fluorescence measurements with a single optical fiber. Applied Optics, vol. 42, No. 13, May 2003, pp. 2436-2442.

Dorshow. R.B. et al. Noninvasive fluorescence detection of hepatic and renal function. Journal of biomedical optics. Jul. 1998. pp. 340-345. vol. 3, No. 3.

Edwards, A.D. et al. Measurement of hemoglobin flow and blood flow by near-infrared spectroscopy. J. Applied Physiology, 1993, vol. 75, pp. 1884-1889.

Fok et al. Oxygen consumption by lungs with acute and chronic injury in a rabbit model. Intensive care medicine. 2001. pp. 1532-1538. vol. 27.

Geddes, L.A. Cardiovascular devices and their applications. Chapter 4: The measurement of cardiac output and blood flow. 1984. pp. 101-120. John Wiley & Sons, New York.

Hollins, B. et al. Fluorometric determination of indocyanine green in plasma. Clinical chemistry. 1987. pp. 765-768. vol. 33, No. 6.

Iijima T. et al. Cardiac output and circulating blood volume analysis by pulse dye densitometry. Journal of Clinical Monitoring, vol. 13, pp. 81-89, 1997.

Nihon Kohden. website: http://kohden.co.jp/intl/ppms-ddg2001.html. Website viewed May 17, 2001.

Preckel, B. et al. Effect of dantrolene in an in vivo and in vitro model of myocardial reperfusion injury. Acta Anaesthesiol Scand. 2000. pp. 194-201. vol. 44.

Sakka, G. et al. Comparison of Cardiac Output and Circulatory Blood Volumes by Transpulmonary Thermo-dye Dilution and Transcutaneous Indocyanine Green Measurement in Critically Ill Patients. Feb. 2002. pp. 559-565.Chest vol. 121, No. 2.

Wang, L. et al. MCML—Monte Carlo modeling of light transport in multi-layered tissues. Computer Methods & Programs in Biomedicine, vol. 47, No. 2, pp. 131-146, 1995.

Weersink et al. Noninvasive measurement of fluorophore concentration in turbid media with a simple fluorescence/reflectance ratio technique. Applied Optics, vol. 40, No. 34, Dec. 2001, pp. 6389-6395.

International Search Report for PCT Application No. PCT/US07/10908, International Filing Date, May 4, 2007. Search Report mailed Mar. 5, 2008.

* cited by examiner

METHOD FOR DYE INJECTION FOR THE TRANSCUTANEOUS MEASUREMENT OF CARDIAC OUTPUT

CROSS-REFERENCE TO RELATED APPLICATIONS

This application claims the benefit of earlier-filed U.S. Provisional Patent Application Ser. No. 60/747,401 filed May 16, 2006 entitled "Method for Dye Injection for The Transcutaneous Measurement of Cardiac Output,". This application is also a continuation-in-part of U.S. patent application Ser. No. 10/847,480, filed May 17, 2004, entitled "Measurement of Cardiac Output and Blood Volume by Non-Invasive Detection of Indicator Dilution," which is a Continuation of U.S. patent application Ser. No. 10/153,387, filed May 21, 2002 (now U.S. Pat. No. 6,757,554, issued Jun. 29, 2004) entitled "Measurement of Cardiac Output and Blood Volume by Non-Invasive Detection of Indicator Dilution," which claims priority to U.S. Provisional Application No. 60/292,580, filed May 22, 2001, entitled "Method and Apparatus for Measurement of Cardiac Output and Blood Volume by Non-invasive Detection of Indicator Dilution,". This application is also related to U.S. patent application Ser. No 11/625,184 filed Jan. 19, 2007 entitled "Method and Apparatus for Measurement of Cardiac Output and Blood Volume by Non-Invasive Detection of Indicator Dilution,". The content of all of these applications is incorporated herein by reference.

FIELD OF INVENTION

This application pertains to the detection of parameters of cardiovascular system of a subject.

GENERAL BACKGROUND AND STATE OF THE ART

Cardiac output is a central part of the hemodynamic assessment in patients having heart disease, acute hemodynamic compromise or undergoing cardiac surgery, for example. Cardiac output is a measure of the heart's effectiveness at circulating blood throughout the circulatory system. Specifically, cardiac output (measured in L/min) is the volume of blood expelled by the heart per beat (stroke volume) multiplied by the heart rate. An abnormal cardiac output is at least one indicator of cardiovascular disease.

The current standard method for measuring cardiac output is the thermodilution technique (Darovic, G. O. Hemodynamic monitoring: invasive and noninvasive clinical application. 2nd Ed. W. B. Saunders, 1995). Generally, the technique involves injecting a thermal indicator (cold or heat) into the right side of the heart and detecting a change in temperature caused as the indicator flows into the pulmonary artery.

Typically, the thermodilution technique involves inserting a flow-directed balloon catheter (such as a Swan-Ganz catheter) into a central vein (basilic, internal jugular or subclavian) and guiding it through the right atrium and ventricle to the pulmonary artery. The balloon catheter is typically equipped with a thermistor near its tip for detecting changes in blood temperature. A rapid injection of a bolus of chilled glucose solution (through a port in the catheter located in the vena cava near the right atrium) results in a temperature change in the pulmonary artery detected with the thermistor. The measured temperature change is analyzed with an external electronic device to compute the cardiac output. The algorithm implemented in this computation is typically a variant of the Stewart-Hamilton technique and is based on the theory of indicator mixing in stirred flowing media (Geddes L A, Cardiovascular devices and measurements. John Wiley & Sons. 1984).

Thermodilution measurements of cardiac output are disadvantageous for several reasons. First, placement of the thermodilution balloon catheter is an expensive and invasive technique requiring a sterile surgical field. Second, the catheter left in place has severe risks to the patient such as local infections, septicemia, bleeding, embolization, catheter-induced damage of the carotid, subclavian and pulmonary arteries, catheter retention, pneumothorax, dysrrhythmias including ventricular fibrillation, perforation of the atrium or ventricle, tamponade, damage to the tricuspid values, knotting of the catheter, catheter transection and endocarditis. Third, only specially trained physicianss can insert the balloon catheter for thermodilution cardiac output. Last, thermodilution measurements of the cardiac output are too invasive to be performed in small children and infants.

Another method used for measuring cardiac output is the dye indicator dilution technique. In this technique, a known volume and concentration of indicator is injected into the circulatory flow. At a downstream point, a blood sample is removed and the concentration of the indicator determined. The indicator concentration typically peaks rapidly due to first pass mixing of the indicator and then decreases rapidly as mixing proceeds in the total blood volume (~10 seconds; first pass concentration curve). Further, indicator concentration slowly diminishes as the indicator is metabolized and removed from the circulatory system by the liver and/or kidneys (time depending upon the indicator used). Thus, a concentration curve can be developed reflecting the concentration of the indicator over time. The theory of indicator dilution predicts that the area under the first pass concentration curve is inversely proportional to the cardiac output.

Historically, indicator dilution techniques have involved injecting a bolus of inert dye (such as indocyanine green) into a vein and removing blood samples to detect the concentration of dye in the blood over time. For example, blood samples are withdrawn from a peripheral artery at a constant rate with a pump. The blood samples are passed into an optical sensing cell in which the concentration of dye in the blood is measured. The measurement of dye concentration is based on changes in optical absorbance of the blood sample at several wavelengths.

Dye-dilution measurements of cardiac output have been found to be disadvantageous for several reasons. First, arterial blood withdrawal is time consuming, labor intensive and depletes the patient of valuable blood. Second, the instruments used to measure dye concentrations (densitometer) must be calibrated with samples of the patient's own blood containing known concentrations of the dye. This calibration process can be very laborious and time consuming in the context of the laboratory where several samples must be run on a daily basis. Further, technical difficulties arise in extracting the dye concentration from the optical absorbance measurements of the blood samples.

A variation on the dye-dilution technique is implemented in the Nihon Kohden pulse dye densitometer. In this technique, blood absorbance changes are detected through the skin with an optical probe using a variation of pulse oximetry principles. This variation improves on the prior technique by eliminating the necessity for repeated blood withdrawal. However, as described above, this technique remains limited by the difficulty of separating absorbance changes due to the dye concentration changes from absorbance changes due to changes in blood oxygen saturation or blood content in the volume of tissue interrogated by the optical probe. This method is also expensive in requiring large amounts of dye to create noticeable changes in absorbance and a light source producing two different wavelengths of light for measuring light absorption by the dye and hemoglobin differentially. Even so, the high background levels of absorption in the circulatory system makes this technique inaccurate. Finally, where repeat measurements are desired, long intervals must ensue for the high levels of the indicator to clear from the blood stream. Thus, this technique is inconvenient for patients undergoing testing and practitioners awaiting results to begin or alter treatment.

Other approaches for measuring cardiac output exist which are not based on indicator dilution principles. These include ultrasound Doppler, ultrasound imaging, the Fick principle applied to oxygen consumption or carbon dioxide production and electric impedance plethysmography (Darovic, supra). However, these techniques have specific limitations. For instance, the ultrasound techniques (Doppler and imaging) require assumptions on the three-dimensional shape of the imaged structures to produce cardiac output values from velocity or dimension measurements.

Blood volume measures the amount of blood present in the cardiovascular system. Blood volume is also a diagnostic measure that is relevant to assessing the health of a patient. In many situations, such as during or after surgery, traumatic accident or in disease states, it is desirable to restore a patient's blood volume to normal as quickly as possible. Blood volume has typically been measured indirectly by evaluating multiple parameters (such as blood pressure, hematocrit, etc.). However, these measures are not as accurate or reliable as direct methods of measuring blood volume.

Blood volume has been directly measured using indicator dilution techniques (Geddes, supra). Briefly, a known amount of an indicator is injected into the circulatory system. After injection, a period of time is allowed to pass such that the indicator is distributed throughout the blood, but without clearance of the indicator from the body. After the equilibration period, a blood sample is drawn which contains the indicator diluted within the blood. The blood volume can then be calculated by dividing the amount of indicator injected by the concentration of indicator in the blood sample (for a more detailed description see U.S. Pat. No. 6,299,583 incorporated by reference). However, to date, the dilution techniques for determining blood volume are disadvantageous because they are limited to infrequent measurement due to the use of indicators that clear slowly from the blood.

In the dye dilution method, the dye must be injected as a rapid intravenous bolus, not as a continuous infusion, as the latter does not result in the characteristic dye dilution curve needed for the calculation of cardiac output. Choice of the injection method and volume of the injectate are relevant to measured cardiac output and the variability of sequential measurements of cardiac output obtained with transcutaneous fluorescence dye dilution. The venous system targeted by the injection is characterized by branching veins and venous valves. These present an inherent resistance to injection that contributes to a potential fragmentation of the bolus, as well as to a pooling and delayed release of any residual dye. These can be noted, respectively, by fluctuations in the morphology of the dye dilution curve and a prolongation of the tail of the dye bolus.

SUMMARY

The present cardiovascular measurement devices and methods assess cardiovascular parameters within the circulatory system using indicator dilution techniques. Cardiovascular parameters are any measures of the function or health of a subjects cardiovascular system.

In one aspect of the present cardiovascular measurement devices and methods, a non-invasive method for determining cardiovascular parameters is described. In particular, a non-invasive fluorescent dye indicator dilution method is used to evaluate cardiovascular parameters. The method may be minimally invasive, requiring only a single peripheral, intravenous line for indicator injection into the circulatory system of the patient. Further, a blood draw may not be required for calibration of the system. Further, cardiovascular parameters may be evaluated by measuring physiological parameters relevant to assessing the function of the heart and circulatory system. Such parameters include, but are not limited to cardiac output and blood volume.

Such minimally invasive procedures are advantageous over other methods of evaluating the cardiovascular system. First, complications and patient discomfort caused by the procedures are reduced. Second, such practical and minimally invasive procedures are within the technical ability of most doctors and nursing staff, thus, specialized training is not required. Third, these minimally invasive methods may be performed at a patient's bedside or on an outpatient basis. Finally, methods may be used on a broader patient population, including patients whose low risk factors may not justify the use of central arterial measurements of cardiovascular parameters.

In another aspect of the cardiovascular measurement devices and methods, these methods may be utilized to evaluate the cardiovascular parameters of a patient at a given moment in time, or repeatedly over a selected period of time. The dosages of indicators and other aspects of the method can be selected such that rapid, serial measurements of cardiovascular parameters may be made. These methods can be well suited to monitoring patients having cardiac insufficiency or being exposed to pharmacological intervention over time. Further, the non-invasive methods may be used to evaluate a patient's cardiovascular parameters in a basal state and when the patient is exposed to conditions which may alter some cardiovascular parameters. Such conditions may include, but are not limited to changes in physical or emotional conditions, exposure to biologically active agents or surgery. For example, embodiments of the cardiovascular measurement devices and methods can be used for cardiac output monitoring before, during, or after kidney dialysis; cardiac output monitoring under shock conditions (such as, for example, septic shock, anaphylactic shock, cardiogenic shock, neurogenic shock, hypovolemic shock); cardiac output monitoring during stress tests to better understand the heart's ability to increase blood supply to the heart and body while exercising or under other conditions requiring additional blood flow through the heart; cardiac output monitoring before, during, and after chemotherapy treatment to monitor fluid equilibrium in the body; and cardiac output measurements for athletes needing to understand how their cardiac performance to improve their athletic performance.

In another aspect of the cardiovascular measurement devices and methods, modifications of the method may be undertaken to improve the measurement of cardiovascular parameters. Such modifications may include altering the placement of a photodetector relative to the patient or increasing blood flow to the detection area of the patient's body.

In yet another aspect of the cardiovascular measurement devices and methods, the non-invasive method of assessing cardiovascular parameters utilizes detection of indicator emission, which is fluorescence, as opposed to indicator absorption. Further, indicator emission may be detected in a transmission mode and/or reflection mode such that a broader range of patient tissues may serve as detection sites for evaluating cardiovascular parameters, as compared to other methods. Measurement of indicator emission can be more accurate than measurements obtained by other methods, as indicator emission can be detected directly and independent of the absorption properties of whole blood.

In a further aspect of the cardiovascular measurement devices and methods, a system for the non-invasive or minimally invasive assessment of cardiovascular parameters is described. In particular, such a system may include an illumination source for exciting the indicator, a photodetector for sensing emission of electromagnetic radiation from the indicator and a computing system for receiving emission data, tracking data over time and calculating cardiovascular parameters using the data.

In another aspect of the cardiovascular measurement devices and methods, the methods and system described herein may be used to assess cardiovascular parameters of a variety of subjects. In some embodiments, the methodology can be modified to examine animals or animal models of cardiovascular disease, such as cardiomyopathies. The cardiovascular measurement devices and methods are advantageous for studying animals, such as transgenic rodents whose small size prohibits the use of current methods using invasive procedures. The present cardiovascular measurement devices and methods are also advantageous in not requiring anesthesia which can effect cardiac output measurements.

In yet another aspect of the cardiovascular measurement devices and methods, a noninvasive calibration system can be used to determine the concentration of circulating indicator dye. In some embodiments, the concentration of circulating indicator dye can be determined from the ratio of emergent fluorescent light to transmitted and/or reflected excitation light.

In yet another aspect of the cardiovascular measurement devices and methods, a method for injection of the dye can improve the accuracy of the cardiac measurements. In some embodiments, the injection method comprises intravenous rapid bolus injection of a minimum volume of fluorescent dye followed by a rapid bolus injection of the vehicle without the dye.

In other embodiments of the cardiovascular measurement devices and methods, the methodology can be modified for clinical application to human patients. The present cardiovascular measurement devices and methods may be used on all human subjects, including adults, juveniles, children and neonates.

DETAILED DESCRIPTION

The method and system of the present cardiovascular measurement devices and methods are for the evaluation of cardiovascular parameters of a subject using an indicator dilution technique.

Figure 9:
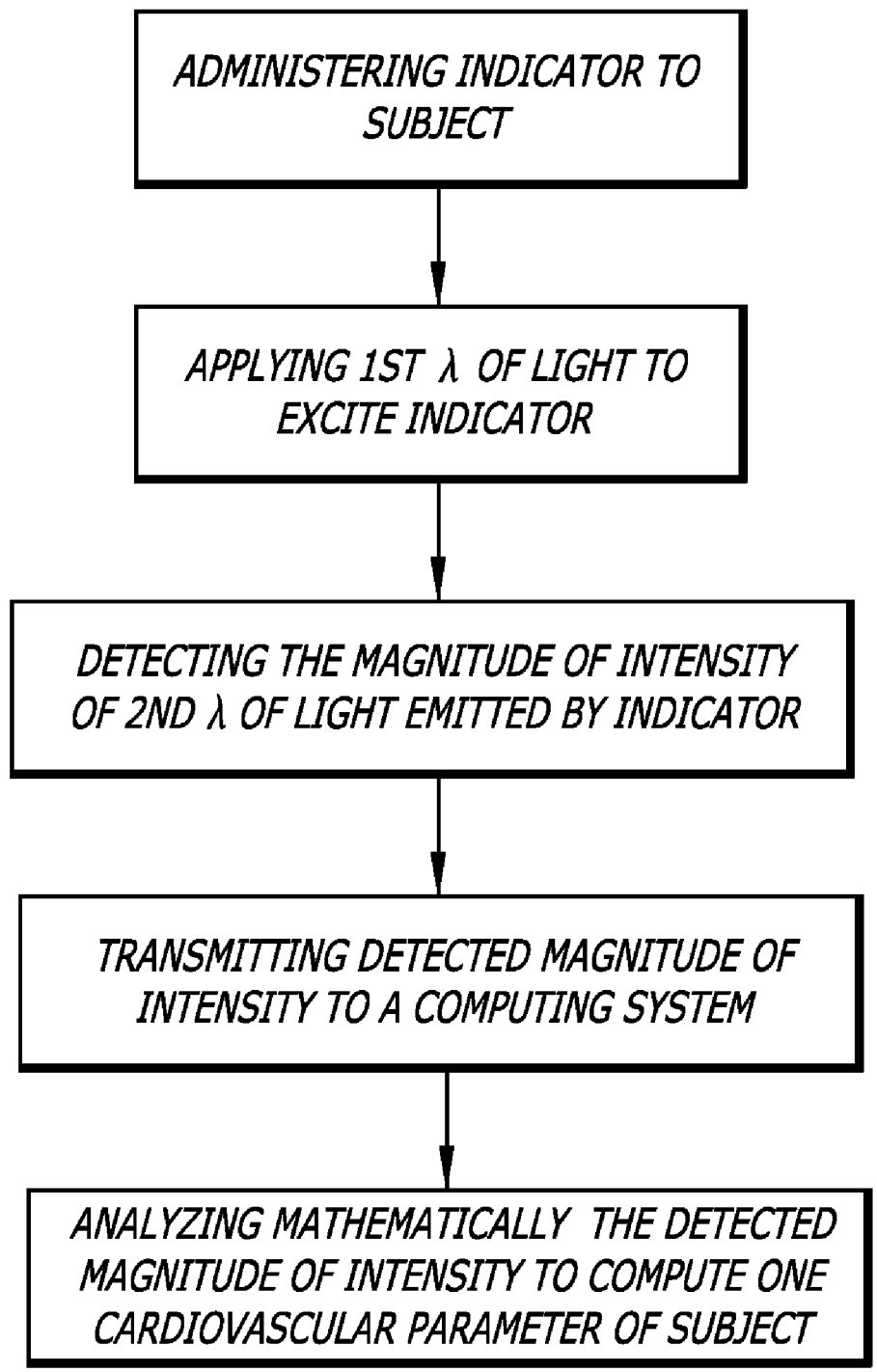
FIG. 9 is a flow chart depicting one exemplary cardiac output measurement.

The method of cardiac output generally involves the injection of a selected amount of indicator into the bloodstream of the subject (FIG. 9). The indicator can be illuminated using a first wavelength of excitation light selected to cause the indicator to fluoresce and emit a second wavelength of light. A photodetector can be placed near the subject for the detection of the intensity of the emitted second wavelength of light, which is proportional to the concentration of the indicator circulating within the circulatory system. The photodetector transmits this intensity information to a computing system, which records and preferably maps the intensity curve of the indicator detected over time.

Typically, the indicator concentration values increase to a peak rapidly after injection of the indicator. Then, the concentration values decrease rapidly, then more steadily as the indicator is mixed throughout the body circulatory system and metabolized over time. A microprocessor driven computation then can calculate from the concentration curve, the patient's cardiac output and/or blood volume values. Additionally, values can be generalized repeatedly using this method, at intervals of about every 2-5 minutes.

Indicators. The indicators useful in the cardiovascular measurement devices and methods may be inert and biocompatible in that they should not alter cardiovascular parameters such as heart rate. Further, the indicator may be a substance that once injected, does not diffuse out of the vasculature of the cardiovascular system. Also, the indicator may be selected to be one which is metabolized within the body at a rate such that repeated measures using this method may be conducted at intervals of about 2-5 minutes. It is also desirable that the background levels of circulating indicator be cleared between intervals, although measurements may be taken when background levels are not zero. Finally, the indicator can be selected to be detectable by the photodetector system selected.

In an exemplary embodiment, a non-invasive dye indicator dilution method may be used to evaluate cardiovascular function function. Many different dye indicators may be used. The dye indicator may be fluorescent, having an excitation wavelength and an emission wavelength in the near infrared spectrum, preferably about 750 nm to about 1000 nm, and more preferably about 750 nm to about 850 nm.

For example, the indicator used may be indocyanine green (ICG; purchased for example from Akorn, Decatur or Sigma, St. Louis, Mo.; commercial names: Diagnogreen©, ICGreen©, Infracyanine©, Pulsion©. ICG has been previously been used to study the microcirculation of the eye, the digestive system and liver function (Desmettre, T., J. M. Devoisselle, and S. Mordon. Fluorescence properties and metabolic features of indocyanine green (ICG) as related to angiography. Surv Ophthalmol 45, 15-27, 2000). ICG fluoresces intensely when excited at near infrared wavelengths. ICG in blood plasma has a peak fluorescence of about 810 to 830 nm with an optimal excitation wavelength of about 780 nm (Hollins, supra; Dorshow, supra). ICG breaks down quickly in aqueous solution, and metabolites are not fluorescent, minimizing recirculation artifact and reducing the time period between which measurements can be made. The wavelength of emission of ICG is also within the optical window (750-1000 nm) in which living tissues are relatively transparent to light.

Other biocompatible fluorescent dyes such as fluorescein and rhodamine would also be suitable in the cardiovascular measurement devices and methods. Fluorescein in blood plasma has a peak fluorescence of about 518±10 nm with an optimal excitation wavelength of about 488 nm (Hollins, supra; Dorshow, supra). Rhodamine in blood plasma has a peak fluorescence of about 640±10 nm with an optimal excitation wavelength of about 510 nm.

Indicator injection and dosage. The dosage of indicator can be selected such that an amount used is non-toxic to the subject, is present in the circulatory system for an amount of time adequate to establish an indicator concentration curve, but is metabolized in an amount of time such that repeated measurements can be conducted at intervals of about 2-5 minutes apart. Further, the indicator can be administered to the subject by injection into a vein.

In one exemplary embodiment, a dosage of about 0.015 mg/kg may be used as this dose leads to peak blood concentrations below 0.002 mg/ml. In this concentration range, the measurement of the circulating indicator concentration is linearly related to the intensity of the emission wavelength detected. For example, in a laboratory animal model, about 0.045 mg can be injected into a 3 kg rabbit (blood volume=200 ml) such that the average circulating concentration is about 0.00023 mg/ml whole blood.

Dye dilution techniques have been applied in humans in other methods and systems using indocyanine green as a dye. Living tissues of humans and animals are relatively transparent for near infrared wavelengths of light which allows for transmission of light across several mm of tissue and transcutaneous detection of the fluorescence emission of ICG. The use of dosages in the ranges stated above is additionally suitable for human use.

Figure 13:
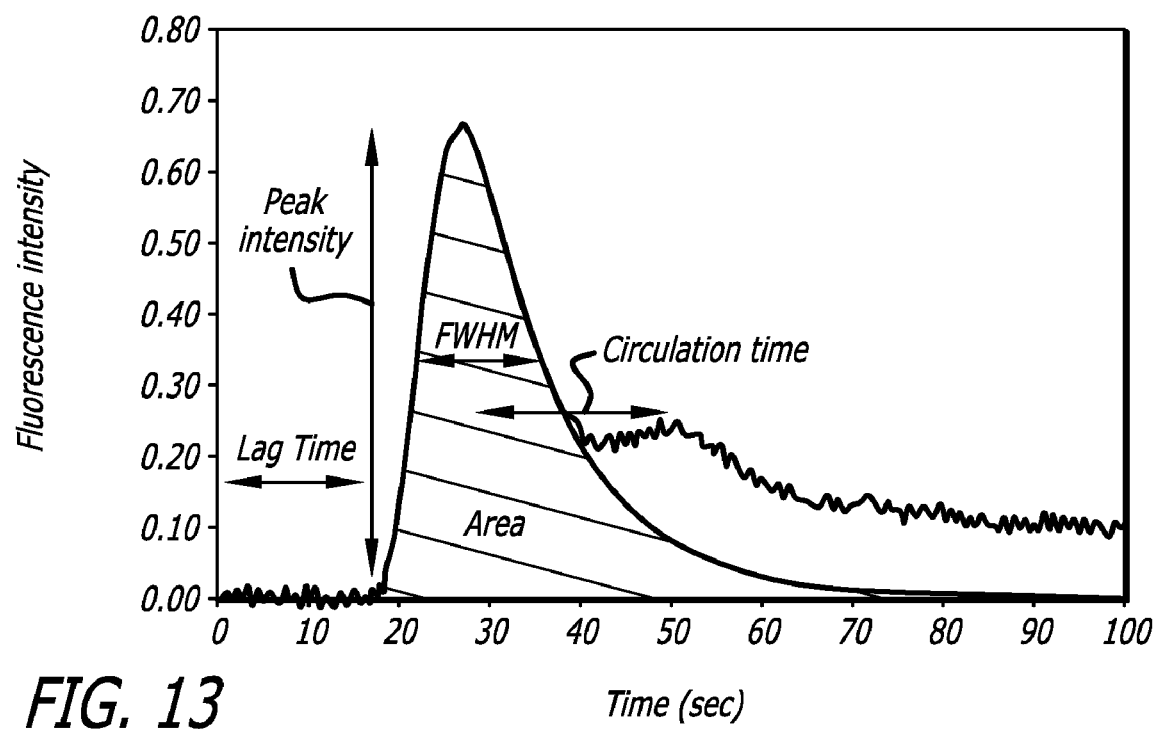
FIG. 13 depicts a graph of a continuous infusion.

In an exemplary embodiment, the injection method comprises intravenous rapid bolus injection of a minimum volume of fluorescent dye followed by a rapid bolus injection of the vehicle (such as saline, for example) without the dye. FIG. 13 depicts a graph of a continuous infusion rather than rapid bolus injection. As shown, an inherent resistance to injection which contributes to a potential fragmentation of the bolus, as well as to a pooling and delayed release of any residual dye. These can be noted, respectively by fluctuations in the morphology of the dye dilution curve and a prolongation of the tail of the dye bolus.

Pooling of the dye is minimized by following the dye injection by an immediate flush with the vehicle. This serves to maintain the dye as a compact bolus and to move the dye out of the slow flow areas of the vessel and into the more rapid flow central venous compartment. The concentration of the dye into a small volume allows the resultant dye dilution peak detected transcutaneously to appear "sharp" and less spread out, i.e. to have a morphology that maximizes amplitude and minimizes the width at half-maximum.

Though, in principal, identical cardiac outputs can be calculated from a sharp or broad dye dilution curves show a greater intertribal variability for the absolute measurements of cardiac output. This is the result of the fact that a broad curve, in particular if there is the appearance of a prolonged tail, reflects a slower dye delivery to the vessel, and an increased susceptibility to dye fragmentation and/or pooling. The prolonged tail overlaps the second pass recirculation of the dye which makes the calculation of the area under the first pass curve inaccurate.

Given the importance of theses tissues a method for injection of the dye for the transcutaneous measurement of cardiac output that is characterized is introduced by all of the following:
a) Intravenous route
b) Concentration of the dye in a minimum volume
c) Rapid bolus administration of the dye
d) Dye administration followed by a rapid bolus injection of the vehicle without the dye In an exemplary embodiment, for an average 70 kg male, the injection method could include administration of a 0.5-5 ml dye bolus over 1-5 seconds, followed by a 3-10 ml bolus of the vehicle over 1-5 seconds. The injection method could be a 1.5 ml injection of the dye, followed by a 3-5 ml flush with the vehicle (physiologic inert solution), each delivered over 1-2 seconds.

The volumes and rates of injection would be expected to be different between application of this method in infants, children and adults, with the doses for infants and children being scaled down when compared to the adult doses. In some embodiments, the dye and the vehicle without the dye could be delivered in separate syringes, through a combination of a syringe and a fluid filled bag, or through a double barrel syringe or single syringe with separate compartments. The injection could either be delivered manually or using an automatic injector. If an automatic injector were employed, injection could be triggered by an external signal such as the subject's respiratory cycle, electrocardiogram or other biologic signal.

In most clinical or biological applications demanding bolus intravenous injection, the speed of injection, the volume of the bolus and whether or not the bolus is followed by a flush is typically not critical. One application where the speed of the injection and the volume of the injectate is important is the thermodilution method. In the thermodilution method, rapid injection may be helpful to obtain optimal signals for the thermodilution curve necessary for the calculation of cardiac output. In the thermodilution method, however, contrary to the dye dilution method, the volume of the injectate may not be too small. A bolus of small volume would result in excessive thermal losses of the injectate prior to reaching the sensing thermistor at the catheter's tip, with a resultant loss of the detected thermodilution signal.

Typical volumes of injection for adults undergoing cardiac output measurement with the thermodilution method are 10 ml of an iced solution, with volumes substantially less resulting in questionable results. This compares to 1.5 ml typically used as the volume of injection for the transcutaneous dye dilution method of measuring cardiac output. Substantially larger volumes may present problems because of the prolonged duration to make such injections into a peripheral vessel and consequent susceptibility of the bolus to pooling and fragmentation.

While the injectate in the thermodilution method is typically delivered with an invasive balloon catheter by an injection port deep in the venous compartment near the right atrium, the injectate in the fluorescence dye dilution method may be delivered through a short (1-2 in) catheter inserted in a peripheral vein.

Illumination Source. The illumination sources useful in cardiovascular measurement devices and methods may be selected to produce an excitation wavelength in the near infrared spectrum, in some embodiments about 750 nm to about 1000 nm, and in other exemplary embodiments about 750 to about 850 nm. This selection is advantageous in at least that most tissues are relatively transparent to wavelengths in this range. Thus, in some embodiments, an indicator in the blood stream is excitable transcutaneously and indicator emissions detected transcutaneously. Further, blood constituents do not fluoresce at these wavelengths, thus there may be no other contributor to the measured fluorescence emission signal. Therefore, this method is advantageous in that at least the sensitivity of detection in this method is improved over other methods, which measure indicator absorption, as opposed to emission.

However, it is within the scope of the cardiovascular measurement devices and methods to use other wavelengths of light, for example in the blue-green or ultraviolet range as some tissues are relatively transparent even at these wavelengths. Selection of the illumination source, therefore, can depend in part on the indicator selected and the tissue from which detection will be made. The illumination source may be selected to result in the peak emission wavelength of the indicator.

Examples of illumination sources which may be used in the cardiovascular measurement devices and methods include, but are not limited to lamps, light emitting diodes (LEDs), lasers or diode lasers.

In some embodiments, modifications to the system or illumination source may be altered to further to maximize the sensitivity or accuracy of the system for measuring indicator concentration. For example, in some embodiments, the excitation wavelength produced by the illumination source will be steady. Alternatively, the excitation wavelength produced by the illumination source can be modulated to allow for a lock-in detection technique.

For example, the illumination source may emit light in a periodic varying pattern having a fixed frequency and the emission recorded by the photodetector read at the same frequency to improve the accuracy of the readings. The periodic varying pattern and frequency can be selected to improve noise-rejection and should be selected to be compatible with the rest of the instrumentation (such as the light source and photodetector).

The illumination source may be adapted to target a detection area of the subject's tissue from which emission wavelength intensity will be recorded. In some embodiments, the illumination source may comprise an optic fiber for directing the excitation light to the detection area. In some embodiments, the illumination source may comprise mirrors, filters and/or lenses for directing the excitation light to the detection area.

Detection Areas. The target detection area is that location of a subject's tissue which is exposed to the excitation wavelength of light and/or from which the emission wavelength light intensity output may be measured.

The method of detection may be non-invasive. In these embodiments, a detection area can be selected such that a photodetector can be placed in proximity to the detection area and emission wavelength light intensity measured. The photodetector may be placed transdermally to at least one blood vessel, and in some embodiments transdermally to a highly vascularized tissue area. Examples of detection areas include, but are not limited to fingers, auricles of the ears, nostrils and areas having non-keratinized epithelium (such as the nasal mucosa or inner cheek). In alternative embodiments, the method of detection is minimally invasive. For example, the photodetector can be placed subdermally (within or beneath the epidermis) and proximate to at least one blood vessel or in a perivascular position.

In yet alternative exemplary embodiments, the method of detection is minimally invasive. For example, the photodetector can be placed intravascularly to detect indicator emissions, such as within an artery. In such embodiments, an external probe for emitting and receiving light may not be needed. For example, in some embodiments the probe may include a fiber optic located within an intravascular catheter. Specifically, the device may include an intravascular catheter made of biocompatible plastic material which contains, embedded in the catheter wall, an optical fiber that ends at or near the tip of the catheter. For example, the catheter may have a diameter of 100 µm or less. The fiber optic can be used to optically sense the presence and concentration of endogenous substances in the blood or exogenous substances injected or infused in the blood stream through the catheter lumen or another catheter. A fiber optic connector at the proximal external end of the fiber optic connects the fiber to an external monitor. In use, the needle of an injection syringe can be inserted through the catheter lumen and used to inject the indicator material (meanwhile the catheter may be allowed to remain within the vein or artery). The injection needle may be withdrawn from the catheter after injection. After the indicator has been injected and the indicator has had sufficient time to circulate through the cardiovascular system, light from a light source can be directed to the blood and circulated indicator via the optical fiber embedded in the catheter. The optical fiber of the catheter may also be used to receive light from the indicator and transmit the light to the monitor. In alternative embodiments, the catheter may include a plurality of optical fibers for transmitting and/or receiving light used to obtain measure parameters of interest of the cardiovascular system. Catheters that include optical fibers are described in U.S. Pat. No. 4,730,622 to Cohen and U.S. Pat. No. 5,217,456 to Narciso, the entire contents of each of which are incorporated by reference. In addition, other sensing devices and mechanisms may be included in the intravascular probe.

Additionally, the detection area may be arterialized during indicator emission detection. Examples of conditions resulting in detection area arterialization include, but are not limited to heating or exposure to biologically active agents which effect sympathetic system blockade (such as lidocaine).

Photodetector. The detection of indicator emissions can be achieved by optical methods known in the art. Measurement of indicator concentration can be made by administering a detectable amount of a dye indicator and using a non-invasive, minimally invasive, or intravascular procedures, preferably for continuous detection. The photodetector may be positioned proximately to the detection area of the subject. The photodetector may be positioned distally or proximately to the site of the illumination source.

Fluorescent light is emitted from the indicator with the same intensity for all directions (isotropy). Consequently, in some embodiments, the emission of the dye can be detected both in "transmission mode" when the excitation light and the photodetector are on opposite sides of the illuminated tissue and in "reflection mode" when the excitation and the photodetector are on the same side of the tissue. This is advantageous over other methods at least in that the excitation light and emitted light can be input and detected from any site on the body surface and not only optically thin structures.

Photodetectors may be selected to detect the quantities and light wavelengths (electromagnetic radiation) emitted from the selected indicator. Photodetectors having sensitivity to various ranges of wavelengths of light are well known in the art.

In some embodiments, modifications to the system are made to further enhance the sensitivity or accuracy of the system for measuring indicator concentration. For example in some embodiments, the detection system can incorporate a lock-in detection technique. For example, the excitation light may be modulated at a specific frequency and a lock-in amplifier can be used to amplify the output of the photodetector only at that frequency. This feature is advantageous in at least that it further improves the sensitivity of the system by reducing signal to noise and allows detection of very small amounts of fluorescence emission.

In some embodiments a photomultiplier tube can be utilized as or operably connected with another photodetector to enhance the sensitivity of the system. Finally, in some embodiments, additional features, such as filters, may be utilized to minimize the background of the emission signals detected. For example, a filter may be selected which corresponds to the peak wavelength range or around the peak wavelength range of the indicator emission.

The detected electromagnetic radiation can be converted into electrical signals by a photoelectric transducing device which is integral to or independent of the photodetector. These electrical signals are transmitted to a microprocessor which records the intensity of the indicator emissions as correlated to the electrical signal for any one time point or over time. (For an example of such a device see U.S. Pat. No. 5,766,125, herein incorporated by reference.)

System Calibration

A) Minimally Invasive Calibration

The method may be minimally invasive in requiring only a single peripheral blood draw from the circulatory system to be taken for calibration purposes. Indicator concentration may be measured continuously and non-invasively using a photodetector. One blood sample from the subject may be withdrawn for calibration of the actual levels of circulating indicator with the indicator levels detected by the system. For example, a blood sample may be drawn from the subject at a selected time after the administration of the indicator into the blood stream. The blood sample may then be evaluated for the concentration of indicator present by comparison with a calibration panel of samples having known indicator concentrations. Evaluation of the indicator concentration may be made spectrophotometrically or by any other means known in the art. Where the subject blood concentration of indicator falls within a range of about 0.001 to about 0.002 mg/ml, the concentration-fluorescence curve is linear and it crosses the origin of the axes, that is the fluorescence is zero when the concentration is zero. Therefore a single measurement point suffices to define the calibration curve, and no further blood samples need be taken.

B) Noninvasive Calibration

In another embodiment no blood draw is required for calibration of this system. It is noted that the fluorescence of some indicators, such as ICG, does not substantially vary from patient to patient and that the skin characteristics are relatively constant for large classes of patients. Thus, the fluorescence in the blood of the patient measured from a given site on the body surface can be converted in an absolute measurement of ICG concentration, once the curve of indicator concentration vs. fluorescence is defined for that site of measurement.

Figure 11A:
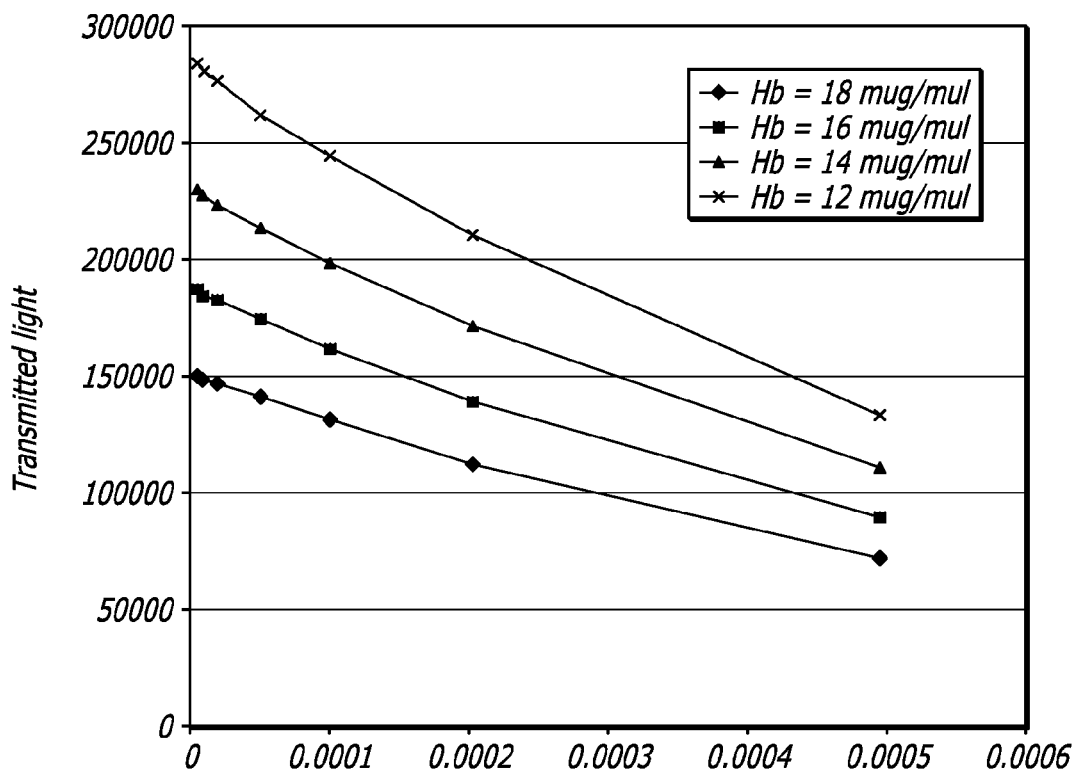
FIGS. 11A-11D are graphs showing calculated transmission and fluorescence signals at 784 nm and 830 nm for different ICG concentrations and hemoglobin contents when absorption coefficients are the same at these two wavelengths.
Figure 11B:
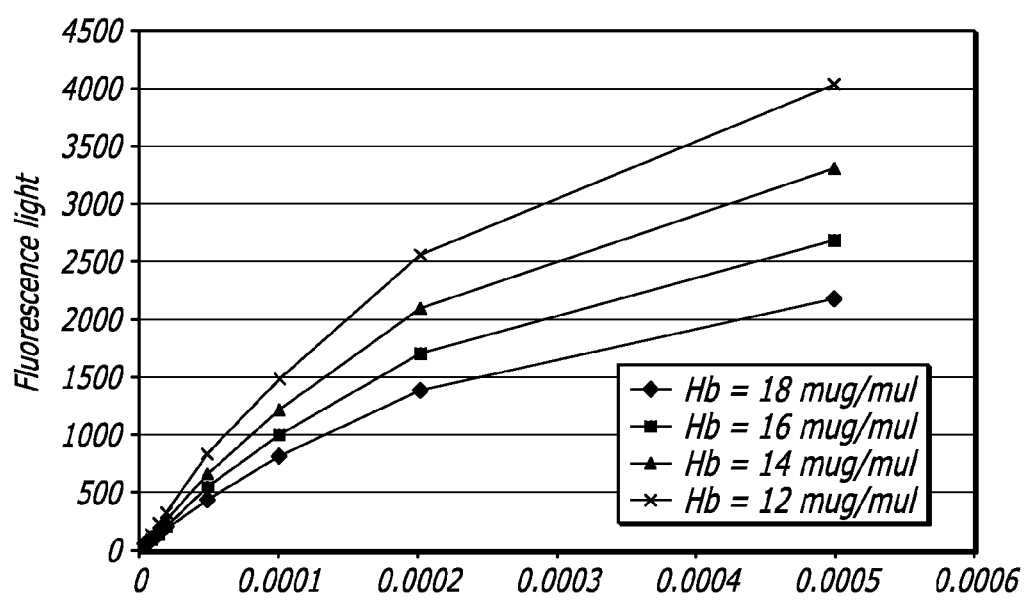
Figure 11C:
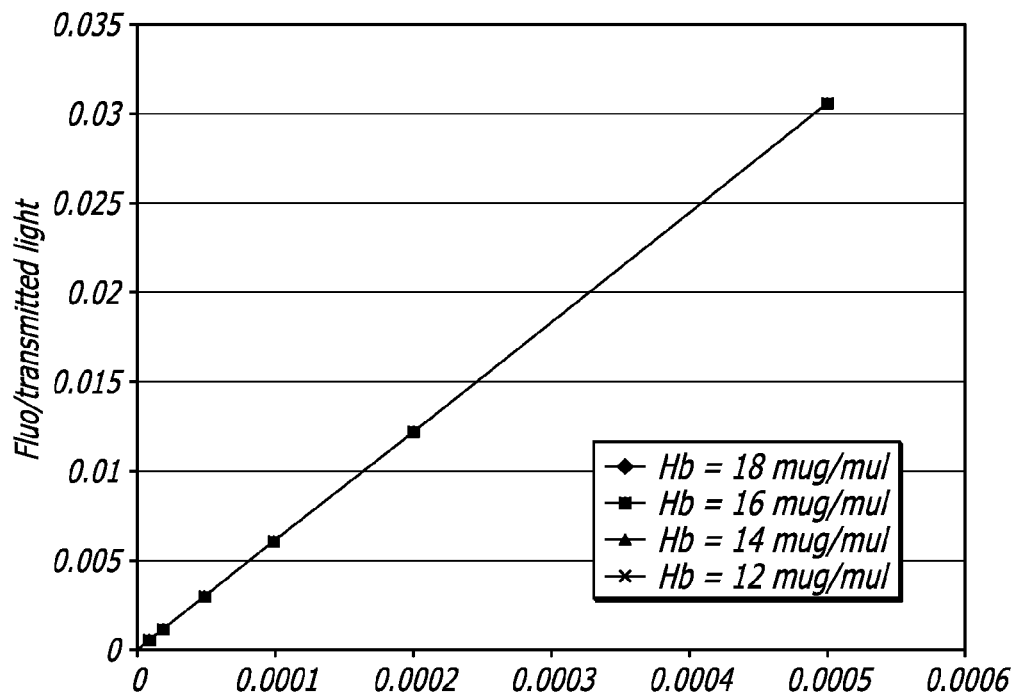
Figure 11D:
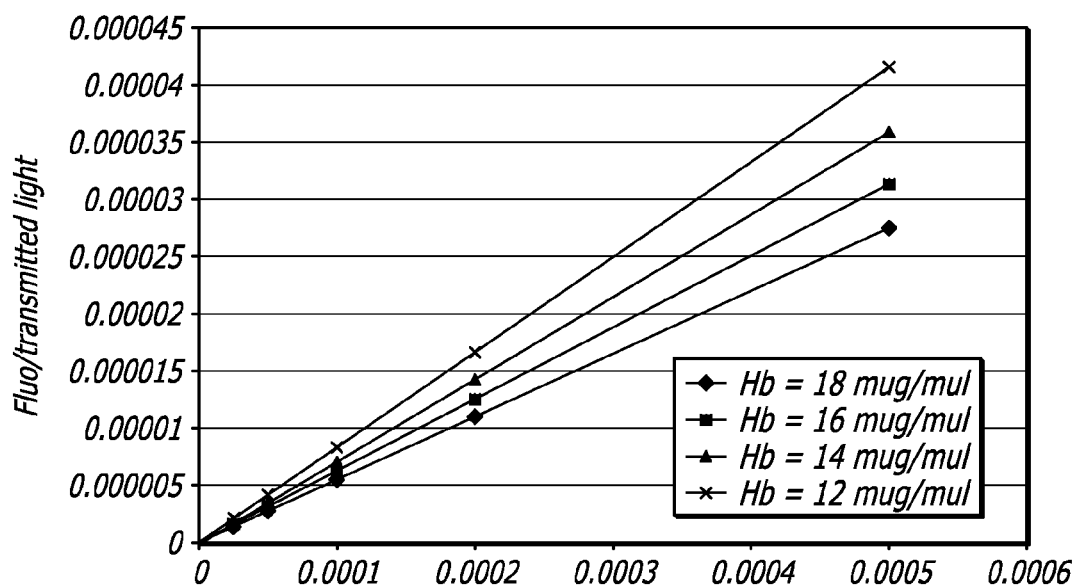

In an exemplary embodiment using noninvasive calibration, the concentration of a fluorescent indicator (ICG) injected in the bloodstream can be determined without taking a blood sample. A probe (including or connected to one or several photodetectors, as described above) can measure the intensity of fluorescent light emitted by the ICG indicator when illuminated by a light source in or near the skin. The probe can also measure the intensity of the light from that source that is reflected by or transmitted through the illumination skin site. Since the ratio of emergent fluorescent light to transmitted excitation light is directly proportional to ICG concentration (see FIGS. 11A-D, FIGS. 12A-12D, and Example 3 below), the concentration of ICG can be determined from the ratio of emergent fluorescent light to transmitted excitation light. For example, the graph in FIG. 11C shows that ICG concentration is directly proportional to the ratio of fluorescent light to transmitted excitation light. In another example illustrated by the graph of FIG. 12C, ICG remains directly proportional to the ratio of fluorescent light to transmitted excitation light even when factoring the variations of absorption properties for hemoglobin (Hb) and ICG with wavelength and the absorption by bloodless tissue. While the slopes of the lines in FIG. 12C vary slightly depending upon hemoglobin content, the differences between the light ratios are relatively small. The ratios may be normalized by creating a table of coefficients that take into account various factors that may affect the light ratios (such as absorption by bloodless tissue, hemoglobin content, path length, skin color, moisture on skin surfaces, body hair, and other factors known to those skilled in the art).

The probe used to transmit and receive light may include a single optical fiber, multiple optical fibers for transmitting and/or receiving light, or other configuration known to those skilled in the art. The excitation light that is received and used in the ratio against fluorescence may be reflected and/or transmitted light. For example, in one embodiment, the light transmitter and receiver can be on the same skin surface so that the receiver can receive light reflected from the tissue. In such an embodiment, the receiving and transmitting element are the same optical fiber (See Diamond et al., "Quantification of fluorophore concentration in tissue-simulating media by fluorescence measurements with a single optical fiber;" *Applied Optics,* Vol. 42, No. 13, May 2003; the contents of which are incorporated herein by reference). In other embodiments, they may be different optical fibers (or other devices known to those skilled in the art). In such embodiments, the various optical fibers may be spatially positioned in relation to each other to optimize measurement, as described in Weersink et al. (See Weersink et al., "Noninvasive measurement of fluorophore concentration in turbid media with a simple fluorescence/reflectance ratio technique;" *Applied Optics,* Vol.

40, No. 34, December 2001; and U.S. Pat. No. 6,219,566 to Weersink et al.; the contents of both of which are incorporated herein by reference). In another embodiment, the transmitter and receiver are positioned substantially opposite each other to allow transmission of the light (such as forward scattering) from the transmitter, through the tissue, and out of the tissue to the receiver on the other side of the tissue.

These methods and systems may be utilized to measure several cardiovascular parameters. Once the system has been calibrated to the subject (where necessary) and the indicator emissions detected and recorded over time, the computing system may be used to calculate cardiovascular parameters including cardiac output and blood volume.

Cardiac output calculations. In some embodiments, the cardiac output can be calculated using equations which inversely correlate the area under the first pass indicator emission curve (magnitude of intensity curve) with cardiac output. Cardiac output is typically expressed as averages (L/min). The general methods have been previously described (Geddes, supra, herein incorporated by reference).

Classically, the descending limb of the curve is plotted semilogrithmically to identify the end of the first pass of indicator. For example, the descending limb of the curve may be extrapolated down to 1% of the maximum height of the curve. The curve can then be completed by plotting values for times preceding the end time. Finally, the area under this corrected curve is established and divided by the length (time) to render a mean height. This mean height is converted to mean concentration after calibration of the detector. The narrower the curve, the higher the cardiac output; the wider the curve, the lower the cardiac output. Several variations of this calculation method are found, including methods that fit a model equation to the ascending and descending portions of the indicator concentration curve.

Depending upon the indicator type and dosage selected, the curve may not return to zero after the end of the first pass due to a residual concentration of indicator recirculating in the system. Subsequent calculations of cardiac output from the curve may then account for this recirculation artifact by correcting for the background emissions, prior to calculating the area under the curve.

Sequential measurements of a cardiovascular circulatory parameter, such as cardiac output or blood volume, may be taken. Each measurement may be preceded by the administration of an indicator to the cardiovascular system. Each measurement may be separated by a time period during which the indicator that was previously administered is substantially eliminated from the circulatory system, for instance by metabolic processes.

To obtain a measurement in absolute physical units, e.g., in liters per minute for cardiac output or liters for blood volume, a blood sample may be taken after each administration of the indicator for calibration purposes, as explained in more detail above.

Another approach may be to take a blood sample only after the first administration of the indicator and to use this blood sample for calibration purposes during each subsequent administration of the indicator and measurement of its resulting fluorescence. However, the operating characteristics of the test equipment may shift during these tests. The optical properties of the tissue being illuminated may also change. The positioning of the illumination source and/or the photo detector may also change. All these changes can introduce errors in the computation of the parameter in absolute physical units when the computations are based on a blood sample that was taken before the changes occurred.

These errors may be minimized by measuring the changes that occur after the blood sample is taken and by then adjusting the measured fluorescence intensity to compensate for these measured changes. This may be accomplished by measuring the intensity of the illumination light after it is transmitted through or reflected by the tissue through which the administered indicator passes. This illumination intensity measurement may be made shortly before, during or shortly after each administration of the indicator. The computations of the cardiovascular parameter that are made during tests subsequent to the first test (when the calibrating blood sample was taken) may then be adjusted in accordance with variations in these illumination intensity measurements.

For example, the computation of the cardiovascular parameter that is made following the second administration of the indicator may be multiplied by the ratio of the illumination intensity measurement made prior to the first administration of the indicator to the illumination intensity measurement made prior to the second administration of the indicator. If the illumination intensity between the first and second measurements doubles, for example, application of this formula may result in a halving of the computation. Other functional relationships between the measured cardiovascular parameter and the illumination intensity measurements may also be implemented.

Any equipment may be used to make the illumination intensity measurements. In one embodiment, the photo detector that detects the fluorescence intensity may also be used to make the illumination intensity measurements. The optical filter that removes light at the illumination frequency may be removed during the illumination intensity measurements. The leakage of the illumination thought this filter may instead be measured and used as the information for the computation.

Another approach to minimizing the number of needed blood samples for a sequence of tests is to take advantage of the known relationship between the amount of indicator that is injected, the volume of blood in the circulatory system and the resulting concentration of the indicator in that blood.

One step in this approach is to determine the volume of blood in the cardiovascular circulatory system using any technique, such as a tracer dilution technique, applied for instance with the Evans Blue dye. The concentration of the indicator after it is administered and mixed throughout the total blood volume, with no offset for metabolic elimination, may then be computed by dividing the amount of the indicator that is administered by the volume of the blood.

Figure 10:
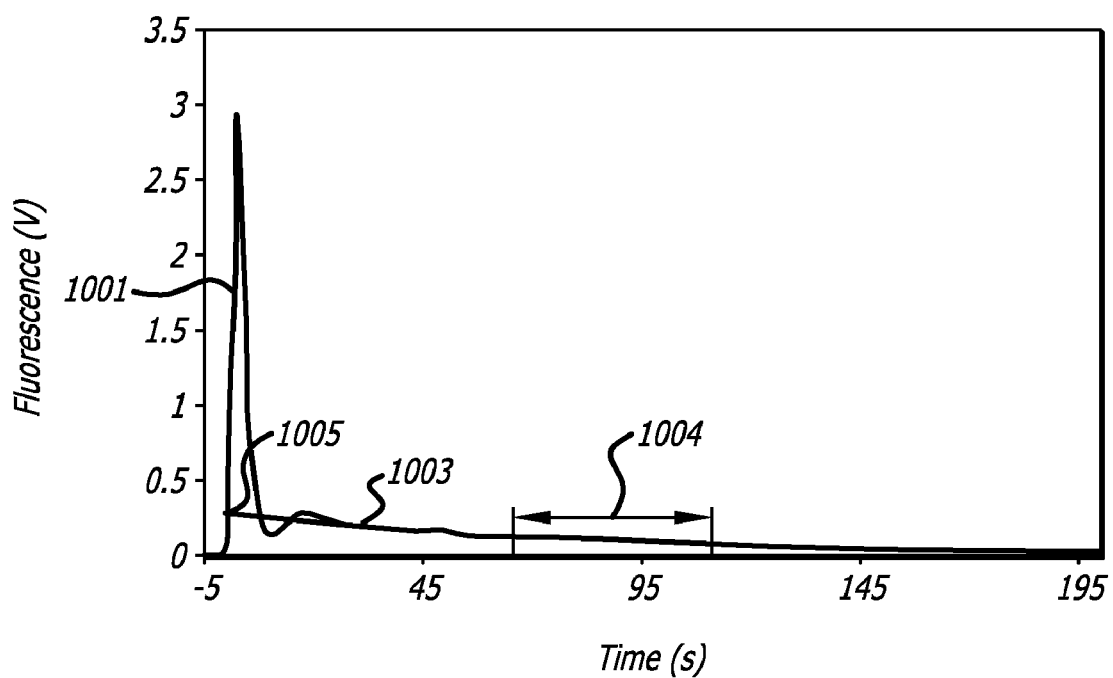
FIG. 10 illustrates a fluorescence intensity curve that includes an extrapolation that intercepts the point on the curve at which the fluorescence is indicative of the concentration of the indicator when mixed throughout the volume of blood of the subject.

The theoretical magnitude of the intensity of the fluorescence from the indicator after the indicator is mixed throughout the total blood volume, without having been metabolized or otherwise eliminated from the circulatory system, may then be determined from the fluorescence curve. FIG. 10 illustrates one way that this may be done. As shown in FIG. 10, the intensity of the fluorescence of an administered indicator will often rise quickly after the injection, as illustrated by a sharply rising portion 1001. The intensity may then decay slowly, as illustrated by a slowly falling portion 1003. A portion of the curve 1004 during the slow decay may be extrapolated until it intercepts a point 1005 on the fast rising portion. The level of the intensity of the fluorescence at the point 1005 may represent the concentration of the indicator after it is administered and mixed throughout the total blood volume, with no offset for metabolic elimination, i.e., the concentration of the indicator that was computed above.

Based on this extrapolated point, a conversion factor may then be determined that converts the measured intensity of the fluorescence to the concentration of the indicator in the cardiovascular system. The conversion factor may be determined by equating it to the ratio of the concentration of the indicator that was calculated above to the measurement of the intensity of the fluorescence at the intercepted point. The concentration of the indicator at other points on the fluorescence intensity curve shown in FIG. 10 may then be computed by multiplying the measured fluorescence intensity value by the conversion factor.

Subsequent administrations of indicator may be made and measured to monitor the cardiovascular parameter over short or long periods of time. The same computational process as is described above may be used each time to determine the absolute physical value of the desired cardiovascular parameter without having to again take a blood sample. The process may also intrinsically compensate for changes between measurements, other than changes in blood volume, such as changes in the operating characteristics of the test equipment, the optical properties of the tissue being illuminated, and/or the positioning of the illumination source and/or the photo detector.

All of the foregoing computations, as well as others, may be automatically performed by a computing system. The computing system may include any type of hardware and/or software.

Results obtained using this system can be normalized for comparison between subjects by expressing cardiac output as a function of weight (CO/body weight (L/min/kg)) or as a function of surface area (cardiac index=CO/body surface area (L/min/m$^2$)).

Blood volume calculations. In some embodiments, blood volume may be measured independently or in addition to the cardiac output. General methods of measuring blood volume are known in the art. In some embodiments, circulating blood volume may be measured using a low dose of indicator which is allowed to mix within the circulatory system for a period of time selected for adequate mixing, but inadequate or the indicator to be completely metabolized. The circulating blood volume may then be calculated by back extrapolating to the instant of injection the slow metabolic disappearance phase of the concentration curve detected over time (Bloomfield, D. A. Dye curves: The theory and practice of indicator dilution. University Park Press, 1974). Alternative methods of calculation include, but are not limited to those described in U.S. Pat. Nos. 5,999,841, 6,230,035 or 5,776,125, herein incorporated by reference.

This method and system may be used to examine the general cardiovascular health of a subject. In one embodiment, the method may be undertaken one time, such that one cardiac output and or blood volume measurement would be obtained. In other embodiments, the method may be undertaken to obtain repeated or continuous measurements of cardiovascular parameters over time. Further, repeated measures may be taken in conditions where the cardiovascular system is challenged such that a subject's basal and challenged cardiovascular parameters can be compared. Challenges which may be utilized to alter the cardiovascular system include, but are not limited to exercise, treatment with biologically active agent which alter heart function (such as epinephrine), parasympathetic stimulation (such as vagal stimulation), injection of liquids increasing blood volume (such as colloidal plasma substitutes) or exposure to enhanced levels of respiratory gases.

Figure 1:
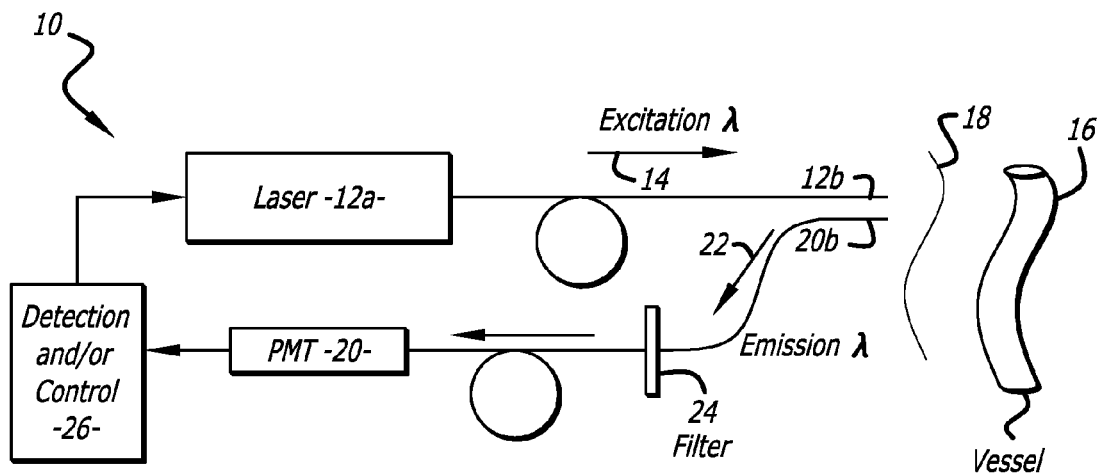
FIG. 1 is a diagrammatic depiction of an example of one embodiment of an exemplary cardiac output measurement system.
Figure 2:
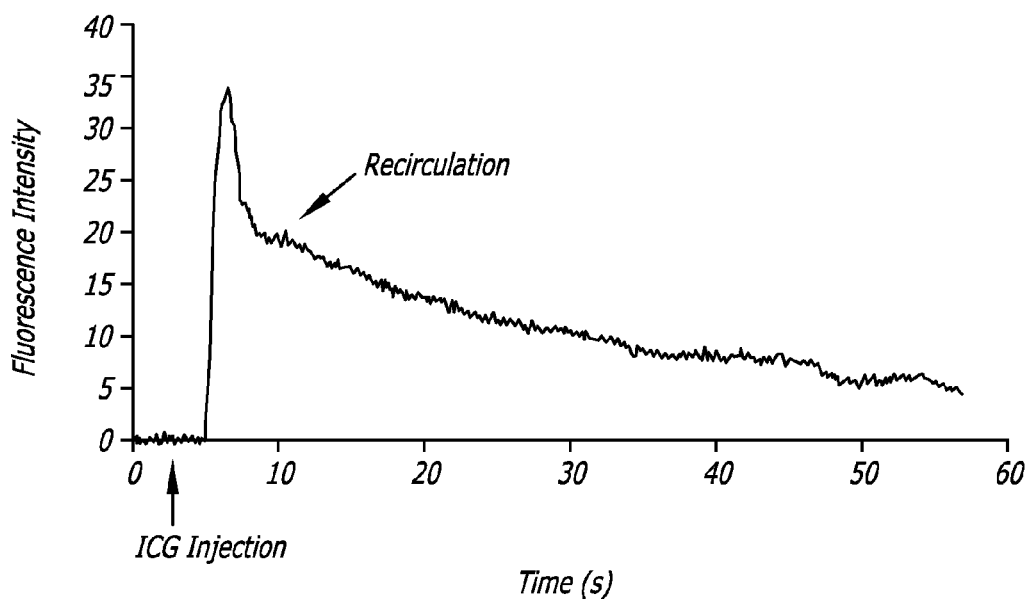
FIG. 2 is a fluorescence intensity curve generated using one embodiment of the cardiovascular measurement devices and methods.
Figure 3:
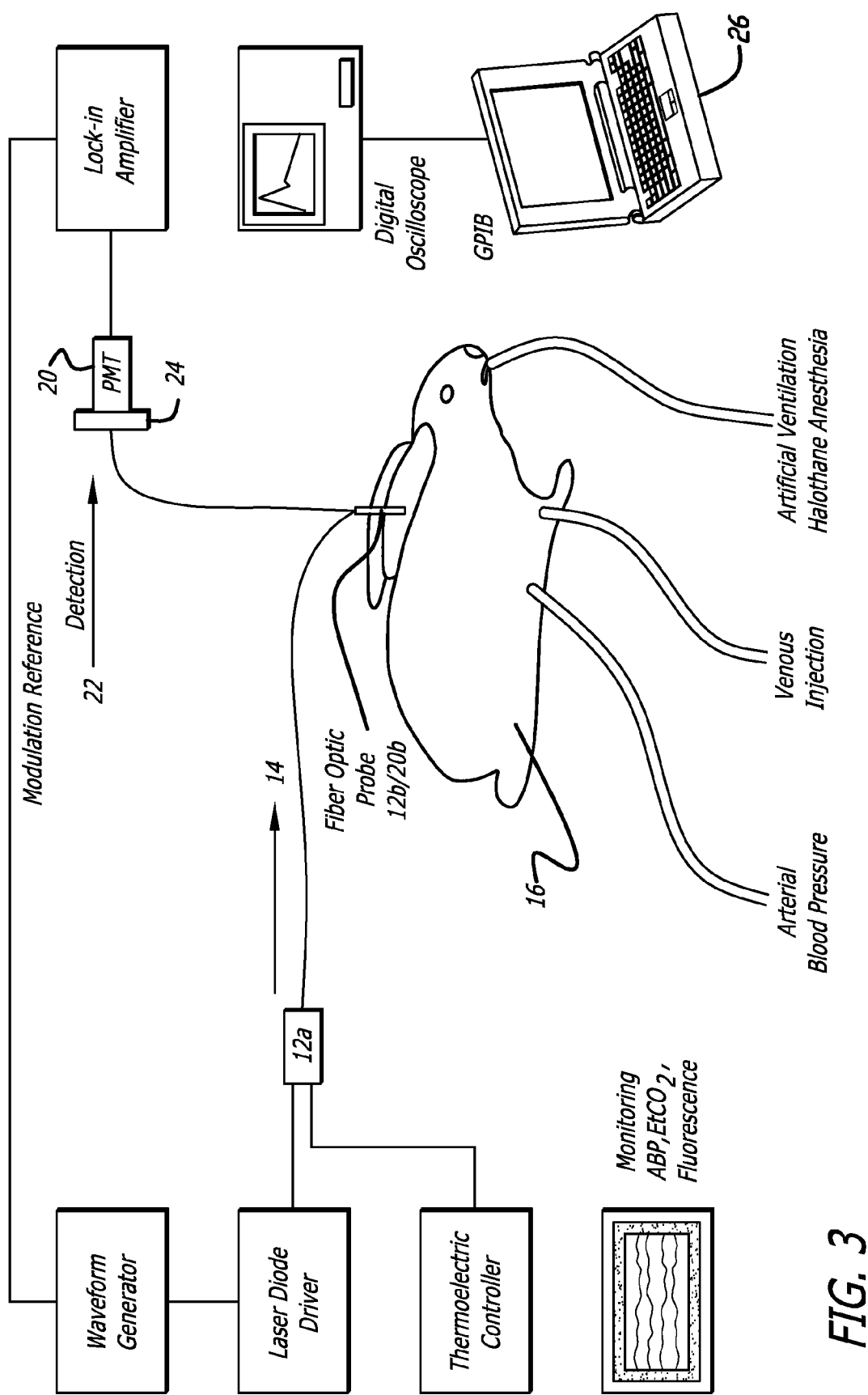
FIG. 3 is a diagrammatic depiction of an example of one embodiment of the cardiovascular measurement device having a photodetector positioned on the ear skin surface.

A schematic of one embodiment of an exemplary system 10 is shown in FIG. 1. The system comprises an illumination source 12 here a 775 nm laser selected to emit a excitation wavelength of light 14 which maximally excites ICG, the indicator selected. Here the illumination source 12 is positioned proximately to the subject 16, such that the excitation wavelength of light 14 is shone transdermally onto the indicator circulating in the bloodstream. The system also comprises a photodetector 20 placed in proximity to the subject's skin surface 18 for detection of the indicator emission wavelength 22. Optionally, a filter 24 may be used for isolating the peak wavelength at which the indicator emits, being about 830 nm. Finally, the photodetector 20 is operably connected to a microprocessor 26 for storing the electronic signals transmitted from the photodetector 20 over time, and generating the indicator concentration curve (FIG. 2). Optionally, the microprocessor 26 may regulate the illumination source to coordinate the excitation and detection of emissions from the indicator, for example using a modulation technique. The microprocessor may also comprise software programs for analyzing the output obtained from the detector 20 such that the information could be converted into values of cardiac output or blood volume, for example and/or displayed in the form of a user interface.

In order to demonstrate the utility of cardiovascular measurement devices and methods, a non-invasive indicator detection system 10 was used to repeatedly monitor cardiac output. With reference to FIG. 1, a fiber optic 12b transmitted light from illumination source 12a to the subject's skin 18. A second fiber optic 20b, positioned near the skin 18 transmitted the emitted light to a photodetector 20. The indicator was intravenously injected. A body portion which included blood vessels near the surface of the skin was irradiated with a laser. A characteristic fluorescence intensity/concentration curve was obtained upon excitation with laser light at about 775 nm and detection of the fluorescence at about 830 nm. From this information cardiac output and blood volume for the subject was calculated.

The system used for this method may comprise a variety of additional components. For example, non-invasive detection is described for monitoring of indicators within the circulatory system of the patient. Modifications of the detectors to accommodate to various regions of the patient's body or to provide thermal, electrical or chemical stimulation to the body are envisioned within the scope of cardiovascular measurement devices and methods. Also, calibration of the system may be automated by a computing system, such that a blood sample is drawn from the patient after administration of the indicator, concentration detected and compared with known standards and/or the emission curve. Also, software may be used in conjunction with the microprocessor to aid in altering parameters of any of the components of the system or effectuating the calculations of the cardiovascular parameters being measured. Further, software may be used to display these results to a user by way of a digital display, personal computer or the like.

The utility of the cardiovascular measurement devices and methods is further illustrated by the following examples, which are not intended to be limiting.

EXAMPLE 1

Experimental system and method. An implementation of the system and method of the cardiovascular measurement devices and methods was tested in rats. The excitation source was a 775 nm pulsed diode laser and the fluorescence was detected with a detector being a photomultiplier (PMT) with extended response in the near-infrared range of the spectrum (FIG. 1). Optic fibers were placed in close contact with the skin of the animal's ear for the excitation and detection of the indicator within the blood stream. After injection of a 100 µl bolus of ICG (0.0075 mg/ml) into the jugular vein of a rat, the fluorescence intensity trace (indicator concentration recording) was measured transcutaneously at the level of the rat's ear using reflection mode detection of emissions (FIG. 2).

Calculation of blood volume and cardiac output. The initial rapid rise and rapid decay segments of the fluorescence intensity trace represent the first pass of the fluorescent indicator in the arterial vasculature of the animal. Such a waveform is characteristic of indicator dilution techniques. This portion of the recording is analyzed with one of several known algorithms (i.e. Stewart Hamilton technique) to compute the "area under the curve" of the fluorescence intensity trace while excluding the recirculation artifact. Here, the initial portion of the fluorescence trace y(t) was fitted with a model equation $y(t)=y_0 t^\alpha \exp(-\beta t)$ which approximates both the rising and descending segments of the trace. This equation derived from a "tank-in-series" representation of the cardiovascular system has been found fit well the experimental indicator dilution recordings. The numerical parameters of the fit were determined from the approximation procedure, and then the "area under the curve" was computed by numeric integration and used to find the cardiac output with the known formula:

$$Q = \frac{m = \text{amount injected}}{\int_0^\infty C(t)\,dt \text{ area under the curve}}$$

Back extrapolation of the slow decay segment of the fluorescence intensity trace to the instant when ICG is first detected in the blood (time 0) yields the estimated concentration of ICG mixed in the whole circulating blood volume. By dividing the amount of injected ICG by this extrapolated ICG concentration at time 0, the circulating blood volume was computed.

Calibration methods. Indicator concentration C(t) was computed from the fluorescence y(t) using one of two calibration methods. Transcutaneous in vivo fluorescence was calibrated with respect to absolute blood concentrations of ICG, using a few blood samples withdrawn from a peripheral artery after bolus dye injection of ICG. The blood samples were placed in a fluorescence cell and inserted in a tabletop fluorometer for measurement of their fluorescence emission. The fluorescence readings were converted into ICG concentrations using a standard calibration curve established by measuring with the tabletop fluorometer the fluorescence of blood samples containing known concentrations of ICG.

An alternative calibration procedure which avoids blood loss uses a syringe outfitted with a light excitation—fluorescence detection assembly. The syringe assembly was calibrated once before the cardiac output measurements by measuring ICG fluorescence in the syringe for different concentrations of ICG dye in blood contained in the barrel of the syringe. During the measurement of cardiac output, a blood sample was pulled in the syringe during the slow decay phase of the fluorescence trace, that is the phase during which recirculating dye is homogeneously mixed in the whole blood volume and is being slowly metabolized. The fluorescence of that sample was converted to concentration using the syringe calibration curve and then related to the transcutaneous fluorescence reading. So long as the ICG concentrations in blood remain sufficiently low (<0.001 mg/ml), a linear relationship can be used to relate fluorescence intensity to concentration.

Either one of these calibration methods can be developed on a reference group of subjects to produce a calibration nomogram that would serve for all other subjects with similar physical characteristics (i.e., adults, small children etc.). This is advantageous over prior methods at least in that an additional independent measurement of the blood hemoglobin concentration for computation of the light absorption due to hemoglobin is not required.

EXAMPLE 2

Figure 4:
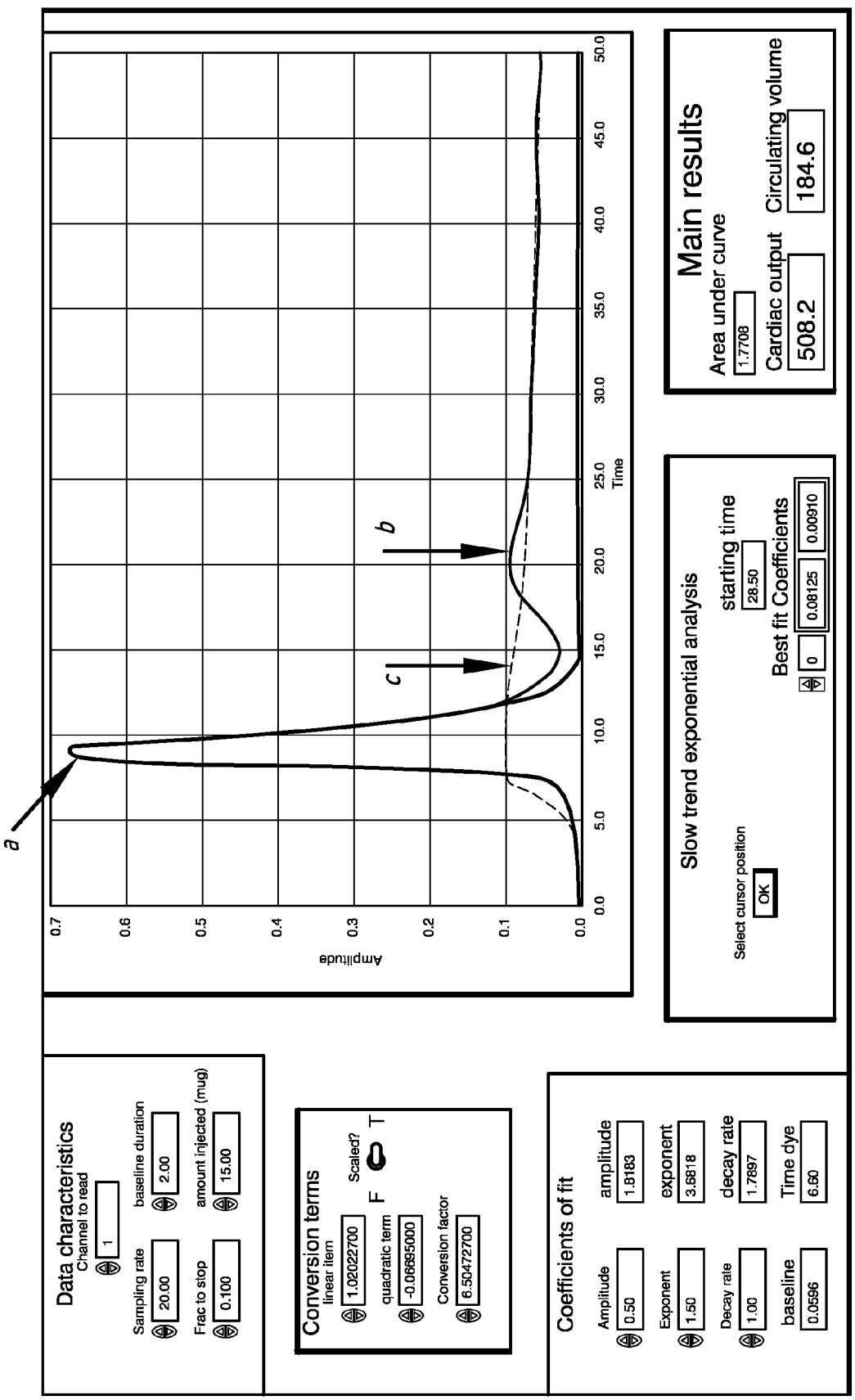
FIG. 4 is a diagrammatic depiction of a user interface of a cardiac output computer program. The interface may depict information regarding values measured and converted from fluorescence to concentration, and parameters of the curve fit for the values obtained using the method or system.

A. A sample method and system for measuring cardiac output and blood volume. Experiments have been performed in New Zealand White rabbits (2.8-3.5 Kg) anesthetized with halothane and artificially ventilated with an oxygen-enriched gas mixture ($Fio_2$~0.4) to achieve a $Sa_{o2}$ above 99% and an end-tidal $Co_2$ between 28 and 32 mm Hg (FIG. 4). The left femoral artery was cannulated for measurement of the arterial blood pressure throughout the procedure. A small catheter was positioned in the left brachial vein to inject the indicator, ICG. Body temperature was maintained with a heat lamp.

Excitation of the ICG fluorescence was achieved with a 780 nm laser (LD head: Microlaser systems SRT-F780S-12) whose output was sinusoidally modulated at 2.8 KHz by modulation of the diode current at the level of the laser diode driver diode (LD Driver: Microlaser Systems CP 200) and operably connected to a thermoelectric controller (Microlaser Systems: CT15W). The near-infrared light output was forwarded to the animal preparation with a fiber optic bundle terminated by a waterproof excitation-detection probe. The fluorescence emitted by the dye in the subcutaneous vasculature was detected by the probe and directed to a 830 nm interferential filter (Optosigma 079-2230) which passed the fluorescence emission at 830±10 nm and rejected the retro-reflected excitation light at 780 nm. The fluorescence intensity was measured with a photomultiplier tube (PMT; such as Hamamatsu H7732-10MOD) connected to a lock-in amplifier (Stanford Research SR 510) for phase-sensitive detection of the fluorescence emission at the reference frequency of the modulated excitation light. The output of the lock-in amplifier was displayed on a digital storage oscilloscope and transferred to a computer for storage and analysis.

In most experiments, one excitation-detection probe was positioned on the surface of the ear arterialized by local heating. In some studies, the laser emission beam was separated in two beams with a beam splitter and directed to two measurement sites (ear skin and exposed right femoral artery). Two detection systems (PMT+lock in amplifier) were used for measurement of the fluorescence dilution traces from the two sites. In all experiments, a complete record of all experimental measurements (one or two fluorescence traces, arterial blood pressure, end-tidal Co2, Doppler flow velocity) was displayed on line and stored for reference.

Calculations. A LabView program was used to control the oscilloscope used for sampling the fluorescence dilution curves, transfer the data from the oscilloscope to a personal computer and analyze the curves online for estimation of the cardiac output and circulating blood volume. As shown on the program user interface (FIG. 5), the measured fluorescence dilution trace (a) is converted to ICG blood (b) using the calibration parameters estimated as described in the next section of this application and fitted to a model: $C(t)=C_0 t^\alpha \exp(-\beta t)$.

The model fit is performed from the time point for which the fluorescent ICG is first detected to a point on the decaying portion of the trace that precedes the appearance of recirculating indicator (identified from the characteristic hump after the initial peak in the experimental trace). The model equation is used to estimate the "area under the curve" for the indicator dilution trace. The theory of indicator dilution technique predicts that the area under the concentration curve is inversely proportional to the cardiac output (Q): $m/\int_0^\infty C(t)dt$.

where m is the mass amount of injected indicator and c(t) is the concentration of indicator in the arterial blood at time t. The program also fits the slow decaying phase of the measurement to a single exponential to derive the circulating blood volume from the value of the exponential fit at the time of injection. For the experimental ICG trace shown in FIG. 4, the estimated cardiac output is 509 ml/min and the circulating blood volume is 184 ml, in the expected range for a 3 Kg rabbit. This computer program is advantageous in that it improved the ability to verify that the experimental measurements are proceeding as planned or to correct without delay any measurement error or experimental malfunction.

Indicator dosage. In this experiment is was found that a dose of about 0.045 mg injected ICG was optimal in this animal to allow for detection of an intense fluorescence dilution curve and at the same time rapid metabolic disposal of the ICG. Further, with this small dose cardiac function measurements could be performed at about intervals of 4 minutes or less.

Detector placement. Defined fluorescence readings were obtained by positioning the detection probe above the skin surface proximate to an artery or above tissue, such as the ear or the paw arterialized by local heating.

B. Calibration of transcutaneous indicator intensity and circulating indicator concentration.

Calibration of the transcutaneous fluorescence intensity measured at the level of the animals' ear as a function of ICG concentration in blood was performed as follows. A high dose of ICG (1 mg) was injected intravenously and equilibrated homogeneously with the animal's total blood volume in about a one minute period. At equilibrium, the blood ICG concentration resulting from this high dose is several times larger than the peak ICG concentration observed during the low dose ICG injections (0.045 mg) used to measure cardiac output. In this way, a calibration curve was created that accommodated the full range of ICG concentrations observed during the cardiac function measurements.

As the liver metabolizes ICG, the blood ICG concentration decreases back to 0 in about 20 minutes. During that time period, 5 to 8 blood samples (1.5 ml) were withdrawn from the femoral artery and placed in a precalibrated blood cuvette. The fluorescence intensity of the blood in the cuvette was converted to a measurement of concentration using the known standard curve of fluorescence intensity versus ICG concentration established for the cuvette. ICG fluorescence was measured at the level of the ear at the exact time of the blood sample withdrawal. Because ICG is homogeneously equilibrated in the animal's blood volume, when the blood samples are withdrawn, the fluorescence intensity measured at the level of the ear corresponds directly to the ICG blood concentration at the time of the measurement and therefore the ICG concentration determined from the cuvette reading. As this example shows, transcutaneous ICG fluorescence is proportional to blood ICG concentration such that a single blood withdrawal can suffice to find the proportionality factor between the two quantities.

Figure 5:
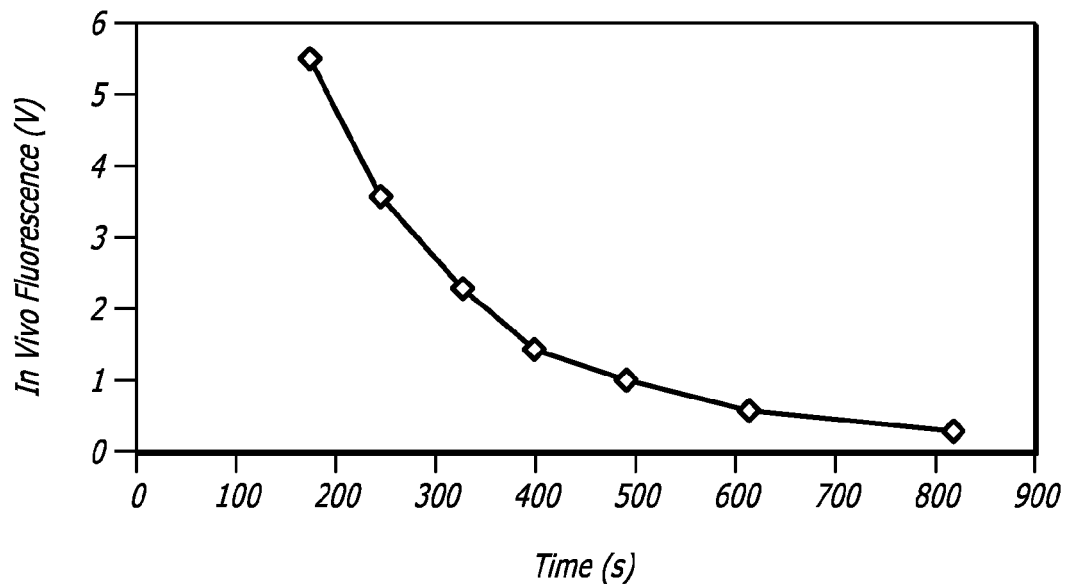
FIG. 5 is a depiction of a decay of fluorescence intensity curve as a function of time following injection of a 1 mg dose of indocyanine green (ICG) in an experimental animal.
Figure 6:
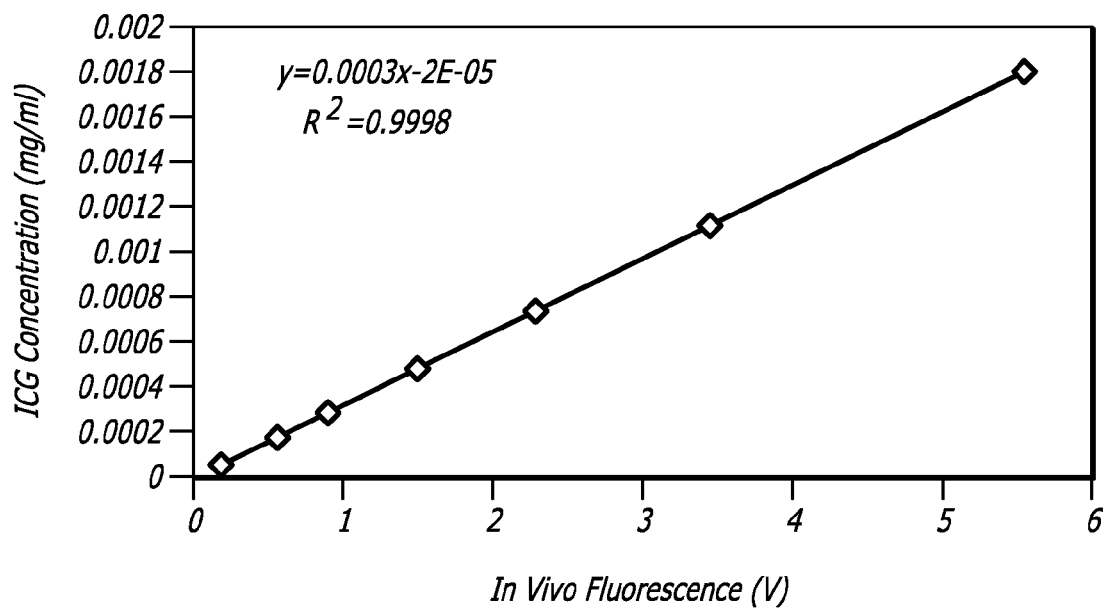
FIG. 6 is a depiction of a calibration curve for blood ICG concentration as a function of transcutaneous ICG fluorescence.

As shown in FIG. 5, the transcutaneous ear fluorescence intensity (in V) as a function of time (in s) after the high dose (1 mg) ICG injection during the calibration sequence. FIG. 5 shows the characteristic first order exponential decay of ICG in blood as the dye is being metabolized. FIG. 6 shows the ICG concentration (in mg/ml) as a function of the in vivo fluorescence for the same example and the same time points. For the range of concentrations used in these studies, ICG concentration and transcutaneous fluorescence were linearly related. The calibration line passes through the origin of the axes since there is no measured fluorescence when the ICG blood concentration is 0.

Thus, a simple proportionality factor exists between blood ICG concentration and transcutaneous fluorescence. This feature of the fluorescence dilution technique measuring light emission is advantageous over the conventional dye dilution technique based on ICG absorption which requires light absorption caused by ICG to be separated from light absorption by tissue and blood. After the proportionality factor is determined, ICG fluorescence dilution profiles can only then be converted into concentration measurements for computation of the cardiac output using the indicator-dilution equation.

Results of cardiac output measurements. Calibrated cardiac output readings have been obtained in 8 animals (body wt: 3.0±0.2 Kg). The following table lists the values during baseline conditions. The values are presented as the mean±standard deviation of three consecutive measurements obtained within a 15 min period.

TABLE 1

| Exp. | Cardiac output (ml/min) |
|---|---|
| 1 | 530 ± 15 |
| 2 | 500 ± 17 |
| 3 | 370 ± 12 |
| 4 | 434 ± 16 |
| 5 | 481 ± 6 |

The average for the five experiments (463 ml/min) is in order of reported cardiac outputs (260-675 ml/min) measured with ultrasound or thermodilution techniques in anesthetized rabbits (Preckel et al. Effect of dantrolene in an in vivo and in vitro model of myocardial reperfusion injury. Acta Anaesthesiol Scand, 44, 194-201, 2000. Fok et al. Oxygen consumption by lungs with acute and chronic injury in a rabbit model. Intesive Care Med, 27, 1532-1538, 2001). Basal cardiac output varies greatly with experimental conditions such as type of anesthetic, duration and depth of anesthesia, leading to the wide range of values found in the literature. In this example, the variability (standard deviation/mean) of the calculated cardiac output with fluorescence dilution is ~3% for any triplicate set of measurements which compares favorable with the reported variability for the thermodilution technique (~5-10%).

C. Comparison of measurements obtained by fluorescence dilution cardiac output method via transcutaneous measurement and subcutaneous measurement.

Experimental methodology. The experimental preparation described in the preceding section (Example 2) includes two measurement sites for the fluorescence dilution traces: a transcutaneous site at the level of the ear central bundle of blood vessels and the exposed femoral artery. The ear vasculature is arterialized by local heating. With this preparation, the cardiac output estimates obtained from the peripheral non-invasive (transcutaneous) measurement site were compared with estimates obtained by interrogating a major artery.

The intensity of the fluorescence signal at the level of the exposed femoral artery during the slow metabolic disappearance phase of the injected ICG is compared to the calibrated ear fluorescence measurement to derive a calibration coefficient (arterial ICG fluorescence into ICG blood concentration). In this way cardiac output estimates expressed in ml/min were derived from the two sites.

Figure 8:
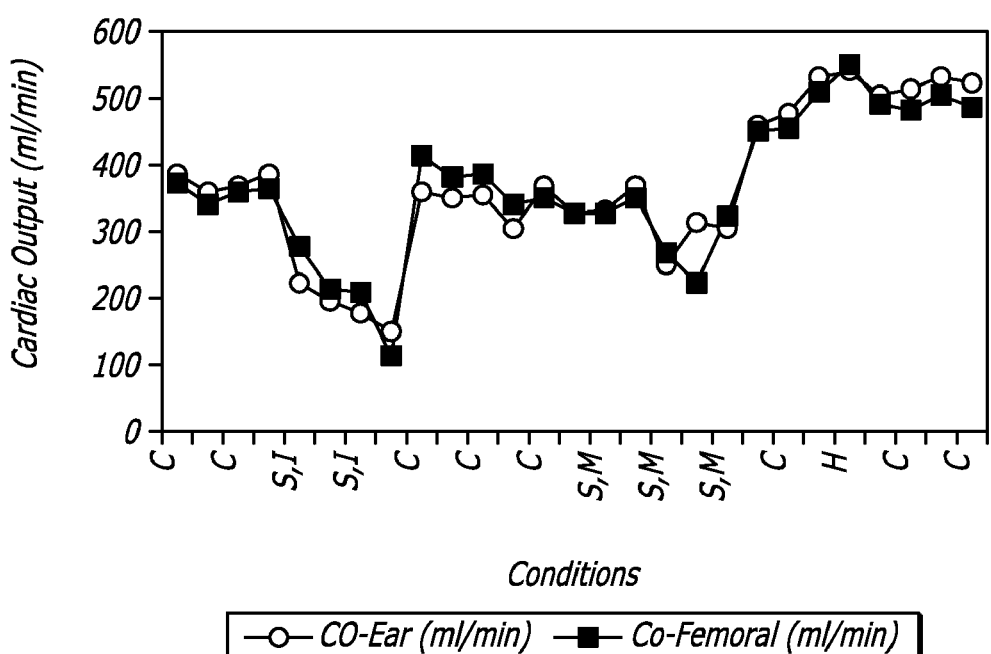
FIG. 8 is a depiction of cardiac output measurements derived from sites on the ear surface and on the exposed femoral artery during one experiment.

Results. FIG. 8 shows the time course of the cardiac output measurements obtained from the ear site and from the exposed femoral artery in a representative experiment during control conditions (C), intense then mild vagal stimulation (S,I and S,M), and post-stimulation hyperemia (H). Near-identical estimates of the cardiac output are obtained from the two sites during all phases of the study.

The relationship between cardiac output derived from measurement of the fluorescence dilution curve at the level of the skin surface ($Co_{skin}$, in ml/min) and at the level of the exposed femoral artery ($Co_{fem}$, in ml/min) was investigated. The linear relationships between the two measures are summarized in the table below:

TABLE 2

| Exp. | Linear regression | Regression Coef. | Number measurements |
|---|---|---|---|
| 1 | $Co_{skin} = 0.65(\pm 0.11) * Co_{fem} + 145.0(\pm 54.0)$ | 0.81 | 22 |
| 2 | $Co_{skin} = 1.01(\pm 0.06) * Co_{fem} + 2.0(\pm 22.0)$ | 0.96 | 27 |
| 3 | $Co_{skin} = 1.05(\pm 0.14) * Co_{fem} - 56.0(\pm 54.0)$ | 0.91 | 13 |

The two measures of fluorescence cardiac output are tightly correlated. In the last two experiments, the slope of the regression line is not statistically different from 1.0 and the ordinate is not different from 0.0 indicating that the two measurements are identical. These observations suggest that fluorescence dilution cardiac output can be reliably measured transcutaneously and from a peripheral site of measurement that has been arterialized by local application of heat. Attenuation of the excitation light and ICG fluorescence emission by the skin does not prevent the measurement of well-defined dye dilution traces that can be analyzed to derive the cardiac output.

D. comparison of measurements obtained by fluorescence dilution cardiac output method and doppler flow velocity technique.

Experimental methodology. The present method was compared with an ultrasonic Doppler velocity probe method to record cardiac output measurements. In this example the above procedure was modified in that, the animal's chest was opened with a median incision of the sternum and a 6 mm 20 MHz Doppler velocity probe was gently passed around the ascending aorta and tightened into a loop that fits snuggly around the aorta.

For detection of the fluorescent detection of the indicator, two illumination+detection fiber optic probes were used: one probe was placed on or above the ear middle vessel bundle and the other probe was placed in proximity to the dissected left femoral artery. Local heating to 42 degrees centigrade arterialized the ear vasculature.

Figure 7:
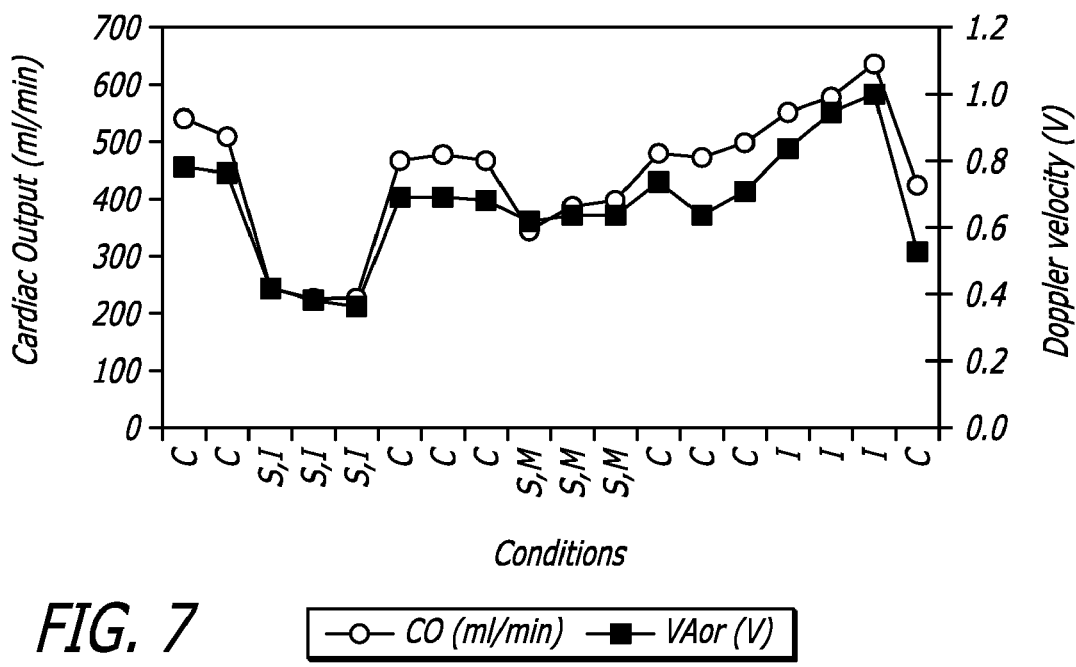
FIG. 7 is a depiction of cardiac output and aortic velocity measurements during one representative experiment.

In this example, two maneuvers were used to change the cardiac output from its control level: vagal stimulation, which reduces the cardiac output, and saline infusion, which increases the circulating volume and cardiac output. The right vagal nerve was dissected to position a stimulating electrode. Stimulation of the distal vagus results in a more or less intense decrease of the heart rate that depends on the stimulation frequency and voltage (1 ms pulses, 3 to 6 V, 10 to 30 Hz). The cardiac output and aortic flow velocity also decrease during vagal stimulation even though less markedly than the heart rate decreases because the stroke volume increases. Saline infusion at a rate of 15-20 ml/min markedly increases the cardiac output. FIG. 7 shows the time course of the cardiac output and aortic velocity measurements in one experiment including control conditions (C), intense then mild vagal stimulation (S,I and S,M), and saline infusion (I).

Results. There is consistent tracking of the Doppler aortic velocity by the fluorescence dilution cardiac output measurement. The relationship between fluorescence dilution cardiac output and aortic Doppler flow velocity was investigated in four rabbits. The linear relationships between fluorescence dilution cardiac output (CO, in ml/min) and aortic flow velocity signal ($VA_{or}$, not calibrated, in Volts) are summarized in the table:

TABLE 3

| Exp. | Linear regression | Regression Coef. | Measurements |
|---|---|---|---|
| 1 | $CO = 789(\pm 123) * VAor + 166(\pm 34)$ | 0.79 | 27 |
| 2 | $CO = 607(\pm 62) * VAor + 50(\pm 32)$ | 0.90 | 24 |
| 3 | $CO = 614(\pm 64) * VAor - 45(\pm 38)$ | 0.90 | 27 |
| 4 | $CO = 654(\pm 41) * VAor - 3(\pm 29)$ | 0.97 | 18 |

This data indicates that the fluorescence dilution cardiac output is highly correlated with aortic flow velocity as indicated by the elevated regression coefficient ($\geq 0.9$ in 3 experiments). Further, the slopes of the linear regression lines between fluorescence dilution cardiac output and aortic flow velocity are similar and statistically not different in the four studies. This suggests a constant relationship between the two variables across experiments. The ordinates of regression lines are not different from 0 in the last three experimental studies, which suggests absence of bias between the two measures of aortic flow.

The results above establish that fluorescence dilution cardiac output measured transcutaneously tracks the Doppler flow velocity measured in the ascending aorta.

EXAMPLE 3

Comparison with Thermodilution Method

Experimental methodology. Other experiments were performed in New Zeeland White rabbits using the methodology described for the preceding example 2. In addition, a 4F thermodilution balloon catheter was inserted into the right femoral vein and advanced until the thermistor reached the main pulmonary artery. Correct placement of the catheter tip was verified visually through the thoracotomy. The catheter was connected to a cardiac output computer to measure the thermodilution cardiac output. Cardiac output measurements were obtained with the present method ($CO_{ICG}$) and the comparison thermodilution method ($CO_{TD}$) during baseline conditions, reduced flow conditions resulting from vagal stimulation, and increased flow conditions resulting from blood volume expansion with saline.

Results. Average values of $CO_{ICG}$ and $CO_{TD}$ measured in baseline conditions in the 10 animals were 412 ($\pm 13$) ml/min and 366 ($\pm 11$) ml/min, respectively, in the expected range for anesthetized rabbits. In each animal, $CO_{ICG}$ was linearly related to $CO_{TD}$ as shown on the following table 4. The slope of the regression line (range: 0.74-1.25) was not different from 1.0 in 8 studies. In the combined data from all 10 studies the linear relationship between $CO_{ICG}$ and $CO_{TD}$ had a slope (0.95$\pm$0.03) not different from 1.0 and an ordinate (77$\pm$10 ml/min) that was slightly >0.

TABLE 4

| Experiment | EQUATION | N | R |
|---|---|---|---|
| 1 | $CO_{ICG} = 0.94^{\dagger}(\pm 0.08) \, CO_{TD} + 84(\pm 23)$ | 21 | 0.94 |
| 2 | $CO_{ICG} = 1.25^{\dagger}(\pm 0.17) \, CO_{TD} - 0^{*}(\pm 39)$ | 17 | 0.88 |
| 3 | $CO_{ICG} = 0.74(\pm 0.11) \, CO_{TD} + 122(\pm 26)$ | 20 | 0.85 |
| 4 | $CO_{ICG} = 0.90^{\dagger}(\pm 0.05) \, CO_{TD} + 98(\pm 15)$ | 11 | 0.99 |
| 5 | $CO_{ICG} = 1.08^{\dagger}(\pm 0.11) \, CO_{TD} + 84(\pm 47)$ | 14 | 0.94 |
| 6 | $CO_{ICG} = 1.07^{\dagger}(\pm 0.09) \, CO_{TD} + 16^{*}(\pm 33)$ | 14 | 0.96 |
| 7 | $CO_{ICG} = 1.15(\pm 0.06) \, CO_{TD} + 29^{*}(\pm 25)$ | 12 | 0.99 |
| 8 | $CO_{ICG} = 0.82^{\dagger}(\pm 0.09) \, CO_{TD} + 83(\pm 37)$ | 12 | 0.94 |
| 9 | $CO_{ICG} = 0.88^{\dagger}(\pm 0.12) \, CO_{TD} + 98^{*}(\pm 62)$ | 16 | 0.89 |
| 10 | $CO_{ICG} = 1.05^{\dagger}(\pm 0.08) \, CO_{TD} - 20^{*}(\pm 33)$ | 15 | 0.97 |
| All | $CO_{ICG} = 0.95^{\dagger}(\pm 0.03) \, CO_{TD} + 74(\pm 10)$ | 152 | 0.94 |

These studies further established that cardiac output $CO_{ICG}$ measured with the present method is linearly related to thermodilution cardiac output $CO_{TD}$. The slope of the regression line between these variables was near 1.0 for most experiments, as well as for the grouped data from all experiments.

EXAMPLE 4

A. Noninvasive Calibration

One embodiment of the calibration system includes a method to determine non-invasively transcutaneously the concentration of a fluorescent indicator injected in the bloodstream by measuring the intensity of the fluorescence light emitted by the indicator when illuminated by a light source in or near the skin and the intensity of the light from that source reflected by or transmitted through the illuminated skin site.

In the pulse dye densitometer (Cardiac output and circulating blood volume analysis by pulse dye densitometry. Iijima T. et al. Journal of Clinical Monitoring, 13, 81-89, 1997, incorporated herein in its entirety by reference), light absorption is measured at two wavelengths: 805 nm where ICG absorption is near maximum and 890 nm where ICG absorption is very small. Assuming at first that tissue absorption of light is only due to blood hemoglobin and ICG, the ratio $C_{ICG}/C_{Hb}$ can be expressed as a function of the ratio $\Psi$ of the optical densities measured at 805 nm and 890 nm, $$C_{ICG}/C_{Hb} = \frac{E_{Hb,805} - \Psi E_{Hb,890}}{\Psi E_{ICG,890} - E_{ICG,805}}$$

where E represents the absorption coefficient from Beer's Law. The latter is expressed as $I_x = I_0 \, e^{-E \cdot C \cdot x}$ with C=concentration, E=absorption coefficient, x=pathlength in substance. Note that if we assume that $E_{ICG},890=0$, the ratio of the concentrations $C_{ICG}/C_{Hb}$ is linearly related to the ratio of the optical densities measured at two wavelengths.

Taking into account scattering and absorption by other material beside ICG and Hb, the developers of the pulse dye densitometer established that the ratio of the optical density changes between before and after ICG administration at 805 nm and 890 nm could be expressed as a function of the ratio $C_{ICG}/C_{Hb}$.

ICG fluorescence is proportional to the absorption of light by ICG at the wavelength of excitation (805 nm in the model above or 784 nm in our studies). Therefore, we hypothesized that the ratio $C_{ICG}/C_{Hb}$ can be derived from the ratio of the change in light signal measured at the wavelength of emission (related to ICG fluorescence) to the light signal measured at the wavelength of excitation (related to ICG and Hb absorption).

We considered a model of light propagation in tissue, which at first assumed that only hemoglobin and ICG were absorbers (See Table 5 below). The absorption coefficients of ICG and Hb were derived from the literature and considered to be independent of wavelength. We then added a dependence of the absorption coefficients on wavelength and tissue absorption in the model to investigate the effect of these factors.

TABLE 5

1-D model of light propagation and fluorescence generation

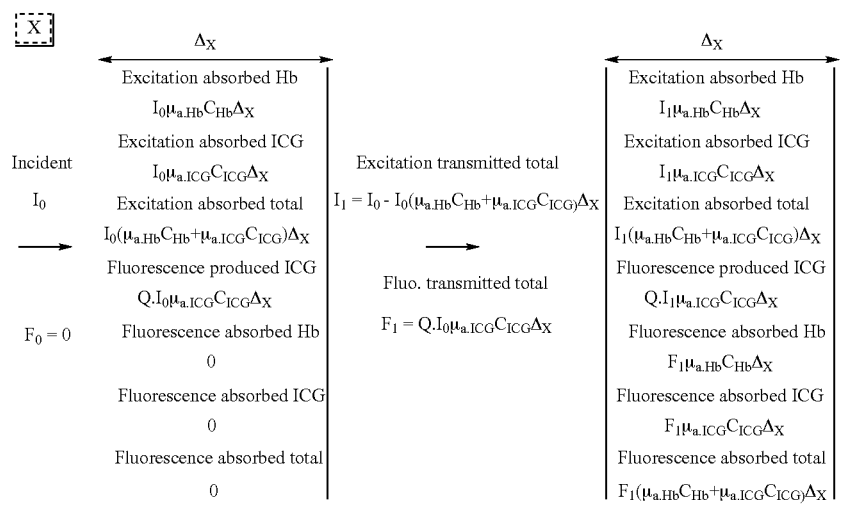

TABLE 5-continued

1-D model of light propagation and fluorescence generation

| [X] | $\Delta_X$ |
|---|---|
| | Excitation absorbed Hb |
| | $I_2 \mu_{a,Hb} C_{Hb} \Delta_X$ |
| Excitation transmitted total | Excitation absorbed ICG |
| $I_2 = I_1 - I_1(\mu_{a,Hb}C_{Hb} + \mu_{a,ICG}C_{ICG})\Delta_X$ | $I_2 \mu_{a,ICG} C_{ICG} \Delta_X$ |
| → | Excitation absorbed total |
| | $I_2(\mu_{a,Hb}C_{Hb} + \mu_{a,ICG}C_{ICG})\Delta_X$ |
| Fluo. transmitted total | Fluorescence produced ICG |
| $F_2 = Q.I_1\mu_{a,ICG}C_{ICG}\Delta_X - F_1(\mu_{a,Hb}C_{Hb}+\mu_{a,ICG}C_{ICG})\Delta_X$ | $Q.I_2\mu_{a,ICG}C_{ICG}\Delta_X$ |
| | Fluorescence absorbed Hb |
| | $F_2\mu_{a,Hb}C_{Hb}\Delta_X$ |
| | Fluorescence absorbed ICG |
| | $F_2\mu_{a,ICG}C_{ICG}\Delta_X$ |
| | Fluorescence absorbed total |
| | $F_2(\mu_{a,Hb}C_{Hb}+\mu_{a,ICG}C_{ICG})\Delta_X$ |

The following data and assumptions were applied to the model of Table 5:

$\mu_{a,ICG} = 38.1$ µl.µg$^{-1}$.mm$^{-1}$ for wavelength $\lambda=784$ nm $\mu_{a,HbO2} \sim \mu_{a,Hb} = 0.0026$ µl.µg$^{-1}$.mm$^{-1}$ for wavelength $\lambda=784$ nm Initially, we assume that the absorption coefficients have the same values at 830 nm (fluorescence) and at 784 nm (incident excitation light).

$C_{Hb} = 12\text{-}18$ g.dl$^{-1}$=120-180 µg/µl in blood $C_{ICG}$ max=0.005 µg/µl in blood Tissue assumed to contain 10% blood Quantum yield of ICG fluorescence=0.04

Transmission calculated through 40 mm tissue in 0.02 mm increment

We modeled transmission and fluorescence signals at 784 nm and 830 nm for different ICG concentrations and hemoglobin contents when absorption coefficients are the same, and the results are illustrated in the graphs of FIGS. 11A-11D. For this simple model, the transmitted excitation light decreases nonlinearly as a function of ICG concentration in the model and the curve varies with the hemoglobin content (see FIG. 11A). Also the emergent fluorescence light increases nonlinearly with ICG concentration (inner filter effect) and the curve varies with hemoglobin content (see FIG. 11B). Thus, the fluorescence signal varies markedly if there is more or less absorption by blood in the tissue.

However, the ratio (emergent fluorescence light/transmitted excitation light) is proportional to the ICG concentration and independent of the hemoglobin content of the tissue (see FIG. 11C). Therefore, by measuring the ratio and if the relationship is known, the ICG concentration can be estimated. Also, the ratio (emergent fluorescence light/transmitted excitation light) is proportional to the ratio (ICG concentration/Hb concentration) but in this case the slope varies with the hemoglobin content of the tissue (see FIG. 11D). In an alternative embodiment of the calibration system, the concentration of Hb may be obtained from a blood sample, and this concentration value can be used to determine the ratio of ICG value to Hb value, which can then be used with the ratio of transmitted excitation light to fluorescence light to determine the concentration of ICG for calibration.

We also modeled transmission and fluorescence signals and at 784 nm and 830 nm for different ICG concentrations and hemoglobin contents when absorption coefficients are the different and an additional absorber is included, and the results are illustrated in the graphs of FIGS. 12A-12D.

Absorption by ICG is actually slightly more elevated at 784 nm (excitation) than it is at 830 nm (fluorescence peak). In contrast oxy-hemoglobin absorption is less at 784 nm (excitation) than it is at 830 nm. In addition to blood hemoglobin and ICG, bloodless tissue absorbs to a certain extent. We determined various values from the literature:

$\mu_{a,ICG} = 38.1$ µl.µg$^{-1}$.mm$^{-1}$ for wavelength $\lambda=784$ nm $\mu_{a,HbO2} \sim \mu_{a,Hb} = 0.0026$ µl.µg$^{-1}$.mm$^{-1}$ for wavelength $\lambda=784$ nm $\mu_{a,ICG} = 34.1$ µl.µg$^{-1}$.mm$^{-1}$ for wavelength $\lambda=830$ nm $\mu_{a,HbO2} \sim \mu_{a,Hb} = 0.0035$ µl.µg$^{-1}$.mm$^{-1}$ for wavelength $\lambda=830$ nm $\mu_{a,tissue} = 0.1$ mm$^{-1}$ independent of wavelength in the range 784-830 nm.

$C_{Hb} = 12\text{-}18$ g.dl$^{-1}$=120-180 µg/ηl in blood $C_{ICG}$ max=0.005 µg/µl in blood Tissue assumed to contain 10% blood Quantum yield of ICG fluorescence=0.04

Transmission calculated through 40 mm tissue in 0.02 mm increment

For this more complete model, the magnitude of the transmitted excitation light and emergent fluorescent lights are markedly decreased when compared to the first model primarily because of the absorption by bloodless tissue. Both signals follow the pattern found for the simple model. In particular, the emergent fluorescence light increases nonlinearly with ICG concentration (inner filter effect) and the curve varies with hemoglobin content.

Figure 12A:
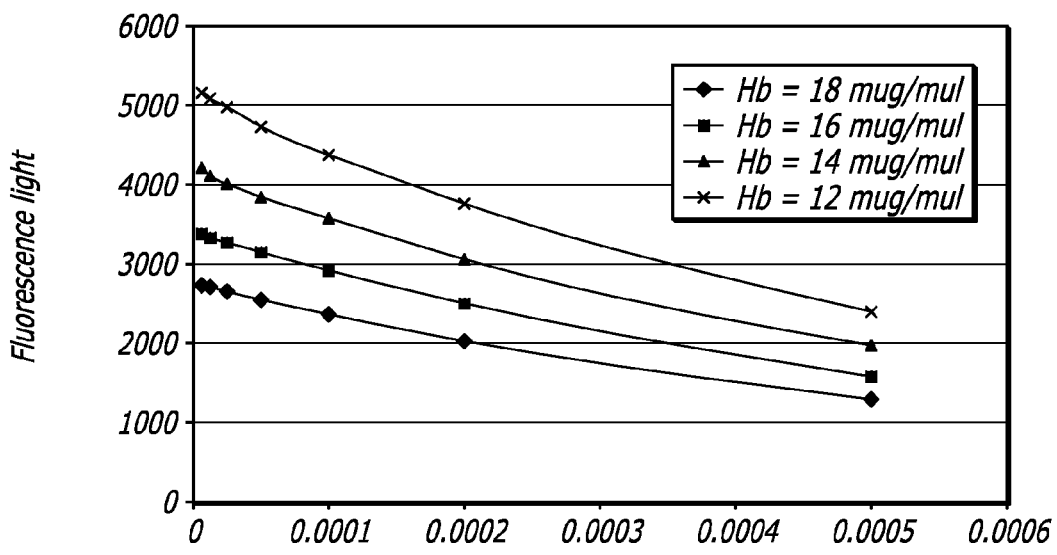
FIGS. 12A-12D are graphs showing transmission and fluorescence signals at 784 nm and 830 nm for different ICG concentrations and hemoglobin contents when absorption coefficients vary with wavelength and an additional absorber is included.
Figure 12B:
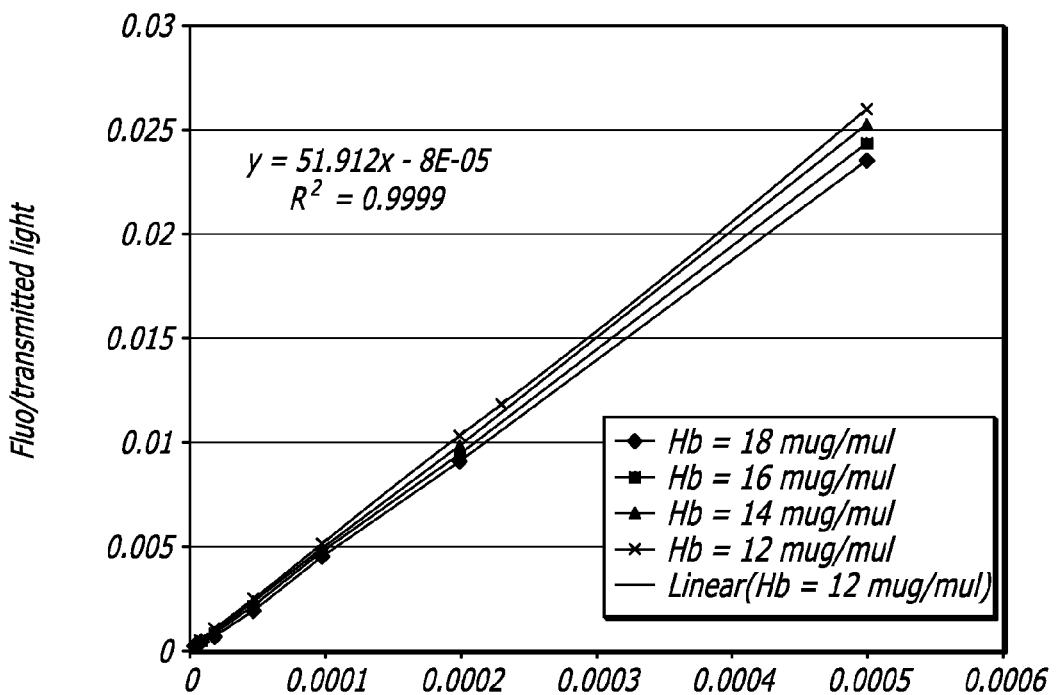
Figure 12C:
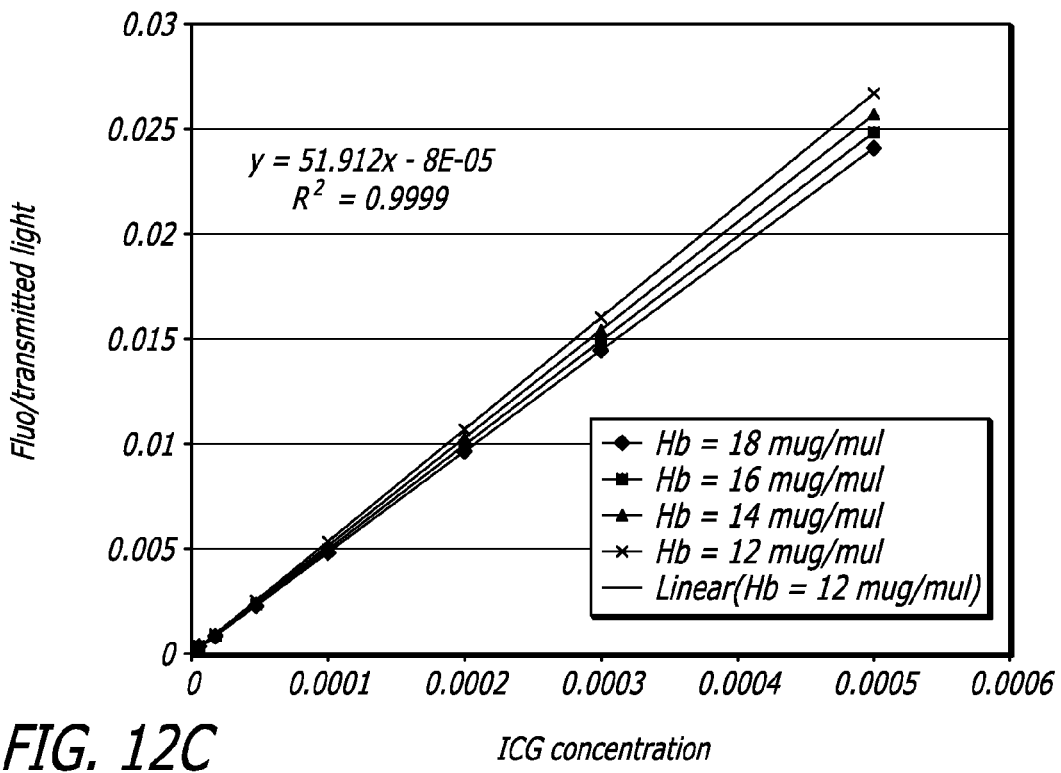
Figure 12D:
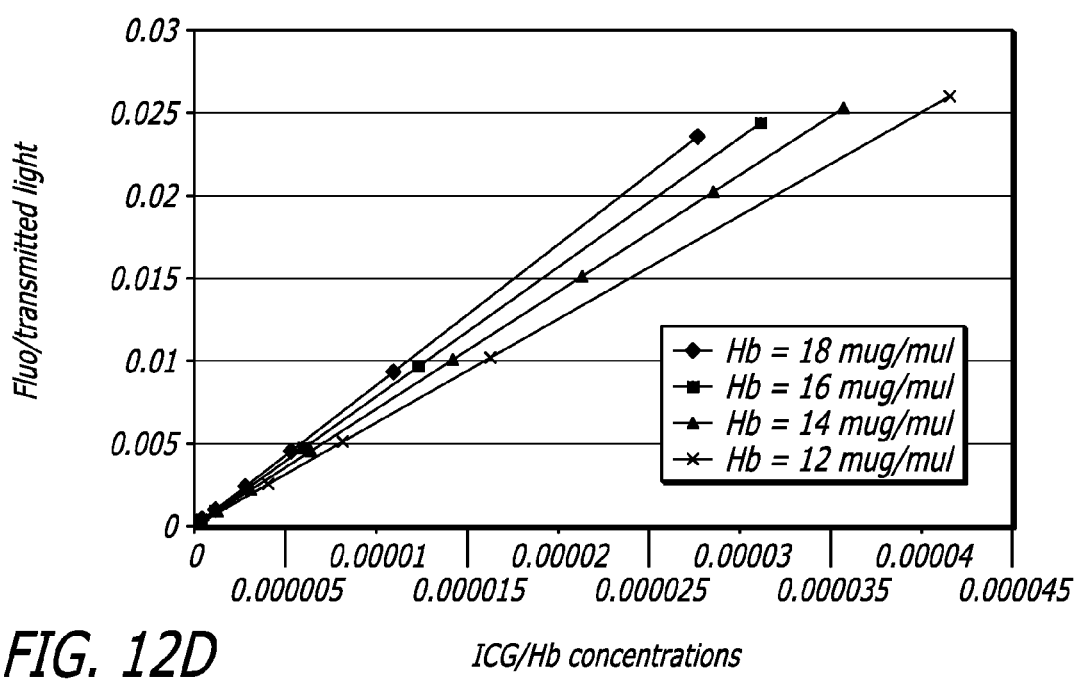

As before the ratio (emergent fluorescence light/transmitted excitation light) is proportional to the ICG concentration (See FIG. 12C). While the slope is dependent on the hemoglobin content, there are only small differences between the four levels of hemoglobin considered. This suggests that by measuring the ratio of the fluorescence/transmitted light, the ICG concentration can be estimated once the linear relationship is determined and possibly including a factor that accounts for the hemoglobin content.

While these models do not consider tissue scattering, the latter is often assumed to increase the pathlength of light in tissue by a fixed proportionality factor: the pathlength factor (about 3.6 for human forearm, see Measurement of hemoglobin flow and blood flow by near-infrared spectroscopy. Edwards A. D. et al.—J. Appl. Physiol. 75, 1884-1889, 1993, the entire contents of which are incorporated herein by reference). This suggests that the model analysis above would likely remain valid even in the presence of scattering.

The previous description of the disclosed embodiments is provided to enable any person skilled in the art to make or use the cardiac output monitor devices, methods and systems. Various modifications to these embodiments will be readily apparent to those skilled in the art, and the generic principles defined herein may be applied to other embodiments without departing from the spirit or scope of the devices, methods and systems described herein. Thus, the cardiac output, devices, methods and systems are not intended to be limited to the embodiments shown herein but are to be accorded the widest scope consistent with the principles and novel features disclosed herein.

The invention claimed is:

1. A method of dye injection for measuring cardiac output of the cardiovascular system of a subject comprising:
   a) preparing a predetermined quantity of a dye solution that can be detected optically by fluorescence when administered into the cardiovascular system of the subject;
   b) preparing a predetermined quantity of a physiologic solution to be administered following the dye solution;
   c) administering the dye solution as a bolus to the cardiovascular system of the subject within a predetermined period; and
   d) administering the physiologic solution as a bolus to the cardiovascular system within a predetermined period subsequent to administration of the dye solution;
   e) calculating the cardiac output of the cardiovascular system based on a proportionality factor that exist between a concentration of the administered dye solution in the cardiovascular system and fluorescence that is transcutaneously detected from the dye solution in the cardiovascular system.

2. The method of claim 1, wherein the quantity of dye solution is within a range 0.5-5 ml.

3. The method of claim 1, wherein the quantity of physiologic solution is within a range 3-5 ml.

4. The method of claim 1, wherein either the dye bolus or the physiologic solution bolus are administered from start to finish within 1-5 seconds.

5. The method of claim 1, wherein the calculating further comprising detecting of dye dilution curve.

6. The method of claim 1, wherein the quantity of the dye solution varies based on the subject's weight.

7. The method of claim 1, wherein the quantity of the dye solution varies based on the subject's age.

8. The method of claim 1, wherein the quantity of the physiologic solution varies based on the subject's weight.

9. The method of claim 1, wherein the quantity of the physiologic solution varies based on the subject's age.

10. The method of claim 1, wherein the dye bolus and the physiologic solution bolus are administered by one or a combination of syringes.

11. The method of claim 1, wherein the dye bolus and the physiologic solution bolus are administered based on a triggering signal.

12. The method of claim 11, wherein the triggering signal is generated based on either the subject's respiratory cycle or an electrocardiogram.

13. The method of claim 1, wherein the dye bolus and the physiological solution bolus are administered by a catheter to the subject's peripheral vein.

* * * * *